United States Patent
Lem et al.

(10) Patent No.: US 12,139,469 B2
(45) Date of Patent: Nov. 12, 2024

(54) AMBER ODORANT

(71) Applicant: FIRMENICH SA, Satigny (CH)

(72) Inventors: George Lem, Satigny (CH); Maud Reiter, Satigny (CH); Alain Boschung, Satigny (CH)

(73) Assignee: FIRMENICH SA, Satginy (CH)

( * ) Notice: Subject to any disclaimer, the term of this patent is extended or adjusted under 35 U.S.C. 154(b) by 746 days.

(21) Appl. No.: 17/420,545

(22) PCT Filed: May 25, 2020

(86) PCT No.: PCT/EP2020/064425
§ 371 (c)(1),
(2) Date: Jul. 2, 2021

(87) PCT Pub. No.: WO2020/239682
PCT Pub. Date: Dec. 3, 2020

(65) Prior Publication Data
US 2022/0106285 A1   Apr. 7, 2022

(30) Foreign Application Priority Data

May 27, 2019  (EP) .................... 19176676

(51) Int. Cl.
*C07D 317/70*   (2006.01)
*C07D 317/64*   (2006.01)

(52) U.S. Cl.
CPC .................. *C07D 317/70* (2013.01)

(58) Field of Classification Search
CPC .................. C07D 317/70; C07D 317/64
USPC .......................... 512/13, 11, 8, 1
See application file for complete search history.

(56) References Cited

U.S. PATENT DOCUMENTS

2016/0090548 A1*  3/2016  Hölscher ............. A61Q 13/00
549/336

FOREIGN PATENT DOCUMENTS

EP   0857723 A1   8/1998

OTHER PUBLICATIONS

International Search Report and Written Opinion for corresponding PCT/EP2020/064425 mailed Jul. 16, 2020, 12 Pages.

* cited by examiner

*Primary Examiner* — Jessica Whiteley
(74) *Attorney, Agent, or Firm* — Armstrong Teasdale LLP

(57) ABSTRACT

Described herein is a compound of formula (I)

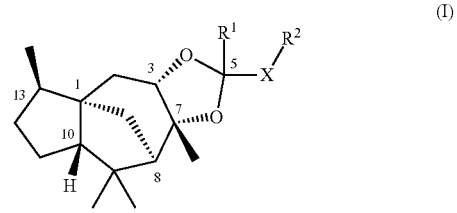

in the form of any one of its stereoisomers or as a mixture thereof, and wherein $R^1$ represents a hydrogen atom, a $C_{1-3}$ alkyl group or $C_{2-3}$ alkenyl group; X represents an oxygen atom when $R^2$ represents a $C_{1-4}$ alkyl group or $C_{2-4}$ alkenyl group or X represents a CH2-O group when $R^2$ represents a $C_{2-4}$ alkenyl group or a MeC=O group. The use as a perfuming ingredient of this compound and this compound as part of a perfuming composition or of a perfuming consumer product are also described.

15 Claims, 1 Drawing Sheet

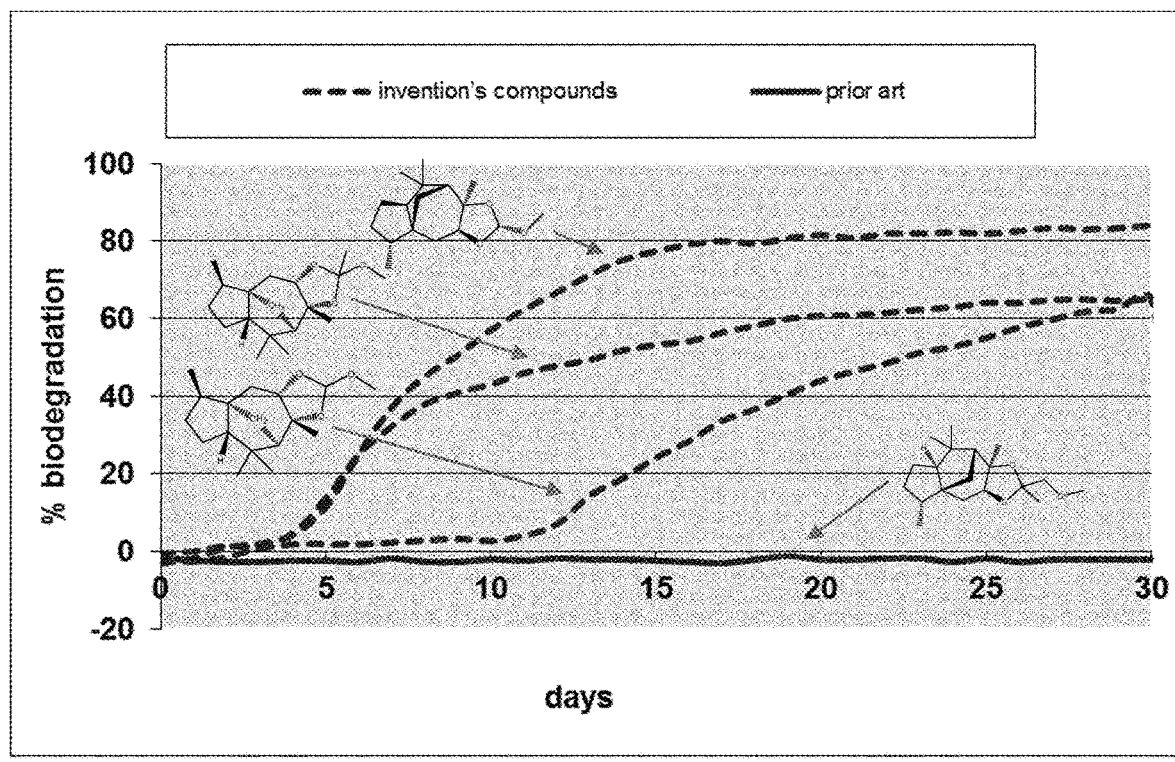

AMBER ODORANT

CROSS-REFERENCE TO RELATED APPLICATIONS

This application is a U.S. National Phase Application of International Patent Application No. PCT/EP2020/064425, filed May 25, 2020, which claims the benefit of priority to European Patent Application No. 19176676.5, filed May 27, 2019, the entire contents of each of which are hereby incorporated by reference herein.

TECHNICAL FIELD

The present invention relates to the field of perfumery. More particularly, it concerns the compound of formula (I) as defined herein below, and its uses as perfuming ingredient. Therefore, following what is mentioned herein, the present invention comprises the invention compound as part of a perfuming composition or of a perfumed consumer product.

BACKGROUND

One of the most sought ingredients in the perfumery field is the one imparting an ambergris impression. Said note, impacting in particular the bottom note by providing more volume and supporting top note of a perfuming composition, is very appreciated and used in a multitude of perfumed consumer products. Originally, Ambergris is a natural product produced in the digestive system of sperm whales which is very rare and very expensive.

So, there is a need to develop a less expensive synthetic alternative to natural ambergris conferring woody and amber odor notes with low volatility to affect the top and the bottom note and being as close as possible to the natural ambergris note also called white amber note while maintaining or even improving the tenacity/substantivity. In the meantime, highly biodegradable novel perfuming ingredients are required in order to minimize the impact on the environment.

US 20160090548 discloses (3aS,4aR,5R,7aS,9R,9aR)-2-(methoxymethyl)-2,5,8,8,9a-pentamethyloctahydro-4H-4a,9-methanoazuleno[5,6-d][1,3]dioxole and (3aS,4aR,5R,7aS,9R,9aR)-2-(methoxymethyl)-5,8,8,9a-tetramethyloctahydro-4H-4a,9-methanoazuleno[5,6-d][1,3]dioxole having ambergris odor. However, said compounds are not biodegradable.

The present invention provides new compounds with the advantages of the prior art while improving the biodegradability. The prior art document mentioned above does not report or suggest any organoleptic properties of the compounds of formula (I), or any use of said compounds in the field of perfumery.

SUMMARY OF THE INVENTION

The invention relates to compound of formula (I) imparting ambergris while being biodegradable.

So, a first object of the present invention is a compound of formula

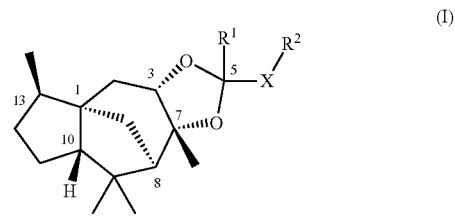

(I)

in the form of any one of its stereoisomers or as a mixture thereof, and wherein $R^1$ represents a hydrogen atom, a $C_{1-3}$ alkyl group or $C_{2-3}$ alkenyl group; X represents an oxygen atom when $R^2$ represents a $C_{1-4}$ alkyl group or $C_{2-4}$ alkenyl group or X represents a CH2-O group when $R^2$ represents a $C_{2-4}$ alkenyl group or a MeC=O group.

A second object of the present invention is the use as perfuming ingredient of a compound of formula (I) as defined above.

A third object of the present invention is a method to confer, enhance, improve or modify the odor properties of a perfuming composition or of a perfumed article, which method comprises adding to said composition or article an effective amount of at least a compound of formula (I) as defined above.

Another object of the present invention is a perfuming composition comprising
i) at least one compound of formula (I), as defined above;
ii) at least one ingredient selected from the group consisting of a perfumery carrier and a perfumery base; and
iii) optionally at least one perfumery adjuvant.

Another object of the present invention is a perfumed consumer product comprising at least one compound of formula (I), as defined above or a perfuming composition as defined above.

A further object of the present invention is a composition of matter comprising
a) 0.1 to 50% w/w of (1R,3S,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane;
b) 10 to 99.9% w/w of compound of formula (I) as defined above; and
c) 20 to 80% w/w of (3R,3aR,6R,7S,8aS)-3,6,8,8-tetramethylhexahydro-1H-3a,7-methanoazulen-5(4H)-one;
the percentage being relative to the total weight of the composition of matter.

BRIEF DESCRIPTION OF THE DRAWINGS

FIG. 1: Biodegradation of (1R,3S,5R,7R,8R,10S,13R)-5-methoxy-7,9,9,13-tetramethyl-4,6-dioxatetracyclo [6.5.1.0$^{1,10}$.0$^{3,7}$]tetradecane (invention's compound), (1R,3S,7R,8R,10S,13R)-5-methoxy-7,9,9,13-tetramethyl-4,6-dioxatetracyclo[6.5.1.0$^{1,10}$.0$^{3,7}$]tetradecane (invention's compound), (1R,3S,7R,8R,10S,13R)-5-methoxy-5,7,9,9,13-pentamethyl-4,6-dioxatetracyclo[6.5.1.0$^{1,10}$.0$^{3,7}$]tetradecane (invention's compound) and (1R,3S,7R,8R,10S,13R)-5-(methoxymethyl)-5,7,9,9,13-pentamethyl-4,6- dioxatetracyclo[6.5.1.0$^{1,10}$.0$^{3,7}$]tetradecane (prior art compound) in function of time.

DESCRIPTION OF THE INVENTION

Surprisingly, it has now been discovered that biodegradable compound of formula (I) imparts a powerful woody and amber note. This compound has also never been disclosed.

A first object of the present invention is a compound of formula

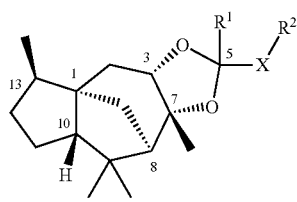

(I)

in the form of any one of its stereoisomers or as a mixture thereof, and wherein R$^1$ represents a hydrogen atom, a C$_{1-3}$ alkyl group or C$_{2-3}$ alkenyl group; X represents an oxygen atom when R$^2$ represents a C$_{1-4}$ alkyl group or C$_{2-4}$ alkenyl group or X represents a CH2-O group when R$^2$ represents a C$_{2-4}$ alkenyl group or a MeC=O group.

Said compounds can be used as perfuming ingredients, for instance to impart odor notes of the woody and amber type.

For the sake of clarity, by the expression "any one of its stereoisomers or as a mixture thereof", or the similar, it is meant the normal meaning understood by a person skilled in the art, i.e. that the invention compound can be a pure or be in the form of a mixture of enantiomers or diastereoisomers (e.g. the carbon 5 could be R, S or a mixture thereof). According to any one of the above embodiments of the invention, the stereocenter of carbon 5 may be R or S or a mixture thereof. The other stereocenters have a fix stereochemistry; i.e. the carbon 1 of compound of formula (I) has an absolute R configuration, the carbon 3 of compound of formula (I) has an absolute S configuration, the carbon 7 of compound of formula (I) has an absolute R configuration, the carbon 8 of compound of formula (I) has an absolute R configuration, the carbon 10 of compound of formula (I) has an absolute S configuration and the carbon 13 of compound of formula (I) has an absolute R configuration. According to any one of the above embodiments of the invention, the compound of formula (I) is in the form of a mixture of isomers comprising at least 55% of isomers with a R configuration on carbon 5 and at most 45% of isomers with a S configuration on carbon 5. Preferably, the compound of formula (I) is in the form of a mixture of isomers comprising at least 70% of isomers with a R configuration on carbon 5 and at most 30% of isomers with a S configuration on carbon 5. Even more preferably, the compound of formula (I) is in the form of a mixture of isomers comprising at least 80% of isomers with a R configuration on carbon 5 and at most 20% of isomers with a S configuration on carbon 5.

For the sake of clarity, when X represents a CH2-O group, the oxygen atom of X is directly linked to R$^2$ group. In other words, when X represents a CH2-O group, the invention compound is of formula

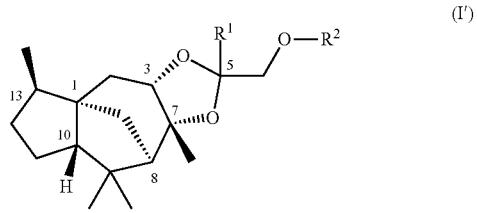

(I')

in the form of any one of its stereoisomers or as a mixture thereof, and wherein R$^1$ and R$^2$ have the same meaning as defined above.

According to any one of the above embodiments of the invention, said compound can be in the form of its E or Z isomer or of a mixture thereof, e.g. the invention comprises compositions of matter consisting of one or more compounds of formula (I), having the same chemical structure but differing by the configuration of the double bond. In particular, compound (I) can be in the form of a mixture consisting of isomers E and Z and wherein said isomer E represents at least 0.5% of the total mixture, or even at least 50% of the total mixture, or even at least 75% (i.e a mixture E/Z comprised between 75/25 and 100/0). Preferably, compound of formula (I) is in the form of an E isomer.

According to any one of the above embodiments of the invention, said compound (I) are C$_{17-24}$ compound, preferably a C$_{17-22}$ compound, even more preferably a C$_{17-19}$ compound.

According to any one of the above embodiments of the invention, X represents an oxygen atom.

According to any one of the above embodiments of the invention, R$^1$ represents a hydrogen atom, a C$_{1-3}$ alkyl group. Preferably, R$^1$ represents a hydrogen atom or a methyl or an ethyl group. Preferably, R$^1$ represents a hydrogen atom or a methyl group. Even more preferably, R$^1$ represents a methyl group.

According to any one of the above embodiments of the invention, R$^2$ represents a C$_{1-4}$ alkyl group or C$_{2-4}$ alkenyl group. Preferably, R$^2$ represents a C$_{1-3}$ linear alkyl group or C$_{2-4}$ linear alkenyl group. Preferably, R$^2$ represents a methyl, an ethyl, a n-propyl, a n-but-1-enyl, a n-prop-1-enyl or a n-prop-2-enyl group. Preferably, R$^2$ represents a methyl, an ethyl or a n-propyl group. Even more preferably, R$^2$ represents a methyl or an ethyl group.

As specific examples of the invention's compounds, one may cite, as non-limiting example, (1R,3S,7R,8R,10S,13R)-5-methoxy-5,7,9,9,13-pentamethyl-4,6-dioxatetracyclo[6.5.1.0$^{1,10}$.0$^{3,7}$]tetradecane or (1R,3S,7R,8R,10S,13R)-5-ethoxy-5,7,9,9,13-pentamethyl-4,6-dioxatetracyclo[6.5.1.0$^{1,10}$.0$^{3,7}$]tetradecane which are characterized by very powerful woody, dry and amber note.

As other example of the invention's compounds, one may cite, as non-limiting example, (1R,3S,7R,8R,10S,13R)-5-methoxy-7,9,9,13-tetramethyl-4,6-dioxatetracyclo[6.5.1.0$^{1,10}$.0$^{3,7}$]tetradecane which possesses an odor similar to the one mentioned above but, slightly less powerful.

As other specific, but non-limiting, examples of the invention's compounds, one may cite the following ones in Table 1:

TABLE 1

Invention's compounds and their odor properties

| Compound structure and name | Odor notes |
|---|---|
| 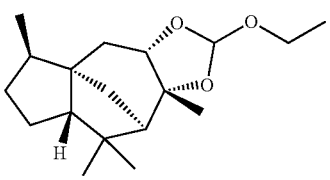<br>(1R,3S,7R,8R,10S,13R)-5-ethoxy-7,9,9,13-tetramethyl-4,6-dioxatetracyclo[6.5.1.0$^{1,10}$.0$^{3,7}$]tetradecane | Dry, woody |
| 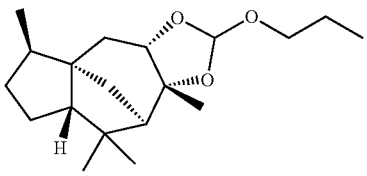<br>(1R,3S,7R,8R,10S,13R)-5-n-propoxy-7,9,9,13-tetramethyl-4,6-dioxatetracyclo[6.5.1.0$^{1,10}$.0$^{3,7}$]tetradecane | Woody, dry |
| 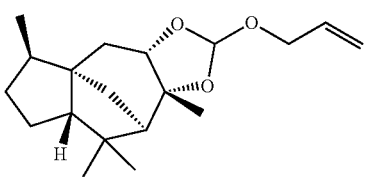<br>(1R,3S,7R,8R,10S,13R)-5-n-prop-2-enoxy-7,9,9,13-tetramethyl-4,6-dioxatetracyclo[6.5.1.0$^{1,10}$.0$^{3,7}$]tetradecane | Woody, dry |
| 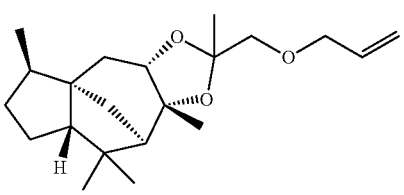<br>(1R,3S,7R,8R,10S,13R)-5-n-but-3-enoxy-7,9,9,13-tetramethyl-4,6-dioxatetracyclo[6.5.1.0$^{1,10}$.0$^{3,7}$]tetradecane | Woody, dry |

TABLE 1-continued

Invention's compounds and their odor properties

| Compound structure and name | Odor notes |
|---|---|
| 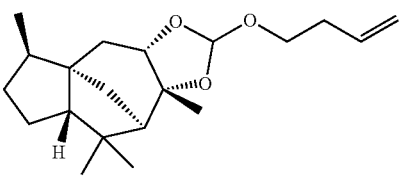<br>(1R,3S,7R,8R,10S,13R)-5-ethoxy-5-ethyl-7,9,9,13-tetramethyl-4,6-dioxatetracyclo[6.5.1.0$^{1,10}$.0$^{3,7}$]tetradecane | Woody, dry |
| 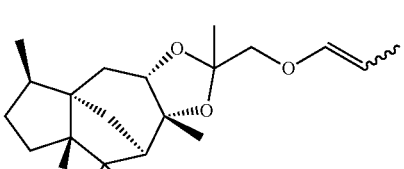<br>(1R,3S,7R,8R,10S,13R)-5-prop-2-enoxy-5,7,9,9,13-pentamethyl-4,6-dioxatetracyclo[6.5.1.0$^{1,10}$.0$^{3,7}$]tetradecane | Woody, dry |
| 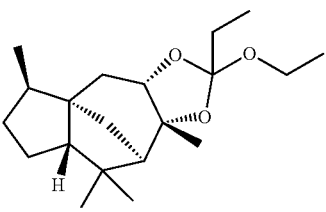<br>(1R,3S,7R,8R,10S,13R)-5-[(allyloxy)methyl]-5,7,9,9,13-pentamethyl-4,6-dioxatetracyclo[6.5.1.0$^{1,10}$.0$^{3,7}$]tetradecane | Woody, dry |
| 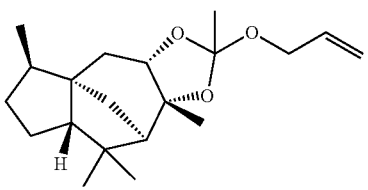<br>(1R,3S,7R,8R,10S,13R)-5,7,9,9,13-pentamethyl-5-{[1-propen-1-yloxy]methyl}-4,6-dioxatetracyclo[6.5.1.0$^{1,10}$.0$^{3,7}$]tetradecane | Woody, dry |

TABLE 1-continued

Invention's compounds and their odor properties

| Compound structure and name | Odor notes |
|---|---|
| 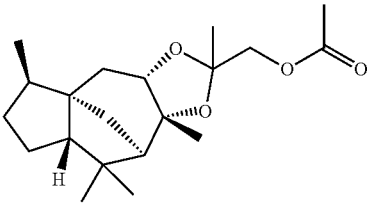<br>(1R,3S,7R,8R,10S,13R)-5,7,9,9,13-pentamethyl-5-{[acetoxy]methyl}-4,6-dioxatetracyclo[6.5.1.0$^{1,10}$.0$^{3,7}$] tetradecane | Woody, dry |

According to any one of the above embodiments of the invention, the compound of formula (I) may be selected from the group consisting of (1R,3S,5R,7R,8R,10S,13R)-5-methoxy-7,9,9,13-tetramethyl-4,6-dioxatetracyclo [6.5.1.0$^{1,10}$.0$^{3,7}$]tetradecane, (1R,3S,5S,7R,8R,10S,13R)-5-methoxy-7,9,9,13-tetramethyl-4,6-dioxatetracyclo [6.5.1.0$^{1,10}$.0$^{3,7}$]tetradecane, or a mixture thereof; (1R,3S, 7R,8R,10S,13R)-5-ethoxy-5,7,9,9,13-pentamethyl-4,6-dioxatetracyclo[6.5.1.0$^{1,10}$.0$^{3,7}$]tetradecane, (1R,3S,7R,8R, 10S,13R)-5-n-prop-2-enoxy-7,9,9,13-tetramethyl-4,6-dioxatetracyclo[6.5.1.0$^{1,10}$.0$^{3,7}$]tetradecane, (1R,3S,7R,8R, 10S,13R)-5-methoxy-5,7,9,9,13-pentamethyl-4,6-dioxatetracyclo[6.5.1.0$^{1,10}$.0$^{3,7}$]tetradecane, (1R,3S,7R,8R, 10S,13R)-5-ethoxy-5-ethyl-7,9,9,13-tetramethyl-4,6-dioxatetracyclo[6.5.1.0$^{1,10}$.0$^{3,7}$]tetradecane, (1R,3S,7R,8R, 10S,13R)-5-ethoxy-7,9,9,13-tetramethyl-4,6-dioxatetracyclo[6.5.1.0$^{1,10}$.0$^{3,7}$]tetradecane, (1R,3S,7R,8R, 10S,13R)-7,9,9,13-tetramethyl-5-n-propoxy-4,6-dioxatetracyclo[6.5.1.0$^{1,10}$.0$^{3,7}$]tetradecane, (1R,3S,7R,8R, 10S,13R)-5-n-but-3-enoxy-7,9,9,13-tetramethyl-4,6-dioxatetracyclo[6.5.1.0$^{1,10}$.0$^{3,7}$]tetradecane, (1R,3S,7R,8R, 10S,13R)-5-[(allyloxy)methyl]-5,7,9,9,13-pentamethyl-4,6-dioxatetracyclo[6.5.1.0$^{1,10}$.0$^{3,7}$]tetradecane, (1R,3S,7R,8R, 10S,13R)-5,7,9,9,13-pentamethyl-5-{[acetoxy]methyl}-4, 6-dioxatetracyclo[6.5.1.0$^{1,10}$.0$^{3,7}$]tetradecane, (1R,3S,7R, 8R,10S,13R)-5-prop-2-enoxy-5,7,9,9,13-pentamethyl-4,6-dioxatetracyclo[6.5.1.0$^{1,10}$.0$^{3,7}$]tetradecane and (1R,3S,7R, 8R,10S,13R)-5,7,9,9,13-pentamethyl-5-{[1-propen-1-yloxy]methyl}-4,6-dioxatetracyclo[6.5.1.0$^{1,10}$.0$^{3,7}$] tetradecane. Preferably, the compound of formula (I) may be selected from the group consisting of (1R,3S,5R,7R,8R,10S, 13R)-5-methoxy-7,9,9,13-tetramethyl-4,6-dioxatetracyclo [6.5.1.0$^{1,10}$.0$^{3,7}$]tetradecane, (1R,3S,5S,7R,8R,10S,13R)-5-methoxy-7,9,9,13-tetramethyl-4,6-dioxatetracyclo [6.5.1.0$^{1,10}$.0$^{3,7}$]tetradecane, or a mixture thereof, (1R,3S, 7R,8R,10S,13R)-5-methoxy-5,7,9,9,13-pentamethyl-4,6-dioxatetracyclo[6.5.1.0$^{1,10}$.0$^{3,7}$]tetradecane and (1R,3S,7R, 8R,10S,13R)-5-ethoxy-5,7,9,9,13-pentamethyl-4,6-dioxatetracyclo[6.5.1.0$^{1,10}$.0$^{3,7}$]tetradecane. Even more preferably, the compound of formula (I) may be (1R,3S,7R, 8R,10S,13R)-5-methoxy-7,9,9,13-tetramethyl-4,6-dioxatetracyclo[6.5.1.0$^{1,10}$.0$^{3,7}$]tetradecane.

When the odor of the invention's compound is compared with the prior art (3aS,4aR,5R,7aS,9R,9aR)-2-(methoxymethyl)-2,5,8,8,9a-pentamethyloctahydro-4H-4a,9-methanoazuleno[5,6-d][1,3]dioxole and (3aS,4aR,5R,7aS,9R, 9aR)-2-(methoxymethyl)-5,8,8,9a-tetramethyloctahydro-4H-4a,9-methanoazuleno[5,6-d][1,3]dioxole as reported in US 20160090548, then the invention's compounds possesses a similar white amber and woody odor reminiscent of Ambergris but distinguishing themselves by woody/limbanol note.

Said differences lend the invention's compounds to be used in a lower concentration than the prior art compounds to impart a similar organoleptic impression.

As mentioned above, the invention concerns the use of a compound of formula (I) as a perfuming ingredient. In other words, it concerns a method or a process to confer, enhance, improve or modify the odor properties of a perfuming composition or of a perfumed article or of a surface, which method comprises adding to said composition or article an effective amount of at least a compound of formula (I), e.g. to impart its typical note. Understood that the final hedonic effect may depend on the precise dosage and on the organoleptic properties of the invention's compound, but anyway the addition of the invention's compound will impart to the final product its typical touch in the form of a note, touch or aspect depending on the dosage.

By "use of a compound of formula (I)" it has to be understood here also the use of any composition containing a compound (I) and which can be advantageously employed in the perfumery industry.

Said compositions, which in fact can be advantageously employed as perfuming ingredients, are also an object of the present invention.

Therefore, another object of the present invention is a perfuming composition comprising:
i) as a perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" it is meant here a material which is practically neutral from a perfumery point of view i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples, solvents such as butylene or propylene glycol, glycerol, dipropyleneglycol and its monoether, 1,2,3-propanetriyl triacetate, dimethyl glutarate, dimethyl adipate 1,3-diacetyloxypropan-2-yl acetate, diethyl phthalate, isopropyl myristate, benzyl benzoate, benzyl alcohol, 2-(2-ethoxyethoxy)-1-ethano, tri-ethyl citrate or mixtures thereof, which are the most commonly used. For the compositions which comprise both a perfumery carrier and a perfumery base, other suitable perfumery carriers than those previously specified, can be also ethanol, water/ethanol mixtures, limonene or other terpenes, isoparaffins such as those known under the trademark Isopar® (origin: Exxon Chemical) or glycol ethers and glycol ether esters such as those known under the trademark Dowanol® (origin: Dow Chemical Company), or hydrogenated castors oils such as those known under the trademark Cremophor® RH 40 (origin: BASF).

Solid carrier is meant to designate a material to which the perfuming composition or some element of the perfuming composition can be chemically or physically bound. In general such solid carriers are employed either to stabilize the composition, or to control the rate of evaporation of the compositions or of some ingredients. Solid carriers are of current use in the art and a person skilled in the art knows how to reach the desired effect. However by way of non-limiting examples of solid carriers, one may cite absorbing gums or polymers or inorganic materials, such as porous polymers, cyclodextrins, wood based materials, organic or inorganic gels, clays, gypsum talc or zeolites.

As other non-limiting examples of solid carriers, one may cite encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- und Geliermittel in Lebensmitteln, Band 2 der Schriftenreihe Lebensmittelchemie, Lebensmittelqualitat, Behr's Verlag GmbH & Co., Hamburg, 1996. The encapsulation is a well-known process to a person skilled in the art, and may be performed, for instance, by using techniques such as spray-drying, agglomeration or yet extrusion; or consists of a coating encapsulation, including coacervation and complex coacervation techniques.

As non-limiting examples of solid carriers, one may cite in particular the core-shell capsules with resins of aminoplast, polyamide, polyester, polyurea or polyurethane type or a mixture thereof (all of said resins are well known to a person skilled in the art) using techniques like phase separation process induced by polymerization, interfacial polymerization, coacervation or altogether (all of said techniques have been described in the prior art), optionally in the presence of a polymeric stabilizer or of a cationic copolymer.

Resins may be produced by the polycondensation of an aldehyde (e.g. formaldehyde, 2,2-dimethoxyethanal, glyoxal, glyoxylic acid or glycolaldehyde and mixtures thereof) with an amine such as urea, benzoguanamine, glycoluryl, melamine, methylol melamine, methylated methylol melamine, guanazole and the like, as well as mixtures thereof. Alternatively one may use preformed resins alkylated polyamines such as those commercially available under the trademark Urac® (origin: Cytec Technology Corp.), Cy Mel® (origin: Cytec Technology Corp.), Urecoll® or Luracoll® (origin: BASF).

Other resins are the ones produced by the polycondensation of an polyol, like glycerol, and a polyisocyanate, like a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate are preferred.

Some of the seminal literature related to the encapsulation of perfumes by polycondensation of amino resins, namely melamine based resins with aldehydes includes articles such as those published by K. Dietrich et al. Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors have enriched the literature in this field and it would be impossible to cover all published developments here, but the general knowledge in encapsulation technology is very significant. More recent publications of pertinence, which disclose suitable uses of such microcapsules, are represented for example by the article of K. Bruyninckx and M. Dusselier, ACS Sustainable Chemistry & Engineering, 2019, vol. 7, pages 8041-805.

By "perfumery base" what is meant here is a composition comprising at least one perfuming co-ingredient.

Said perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin.

In particular one may cite perfuming co-ingredients which are commonly used in perfume formulations, such as:
   Aldehydic ingredients: decanal, dodecanal, 2-methyl-undecanal, 10-undecenal, octanal, nonanal and/or nonenal;
   Aromatic-herbal ingredients: eucalyptus oil, camphor, eucalyptol, 5-methyltricyclo[6.2.1.0~2,7-]undecan-4-one, 1-methoxy-3-hexanethiol, 2-ethyl-4,4-dimethyl-1,3-oxathiane, 2,2,7/8,9/10-Tetramethylspiro[5.5]undec-8-en-1-one, menthol and/or alpha-pinene;
   Balsamic ingredients: coumarin, ethylvanillin and/or vanillin;
   Citrus ingredients: dihydromyrcenol, citral, orange oil, linalyl acetate, citronellyl nitrile, orange terpenes, limonene, 1-p-menthen-8-yl acetate and/or 1,4(8)-p-menthadiene;
   Floral ingredients: methyl dihydrojasmonate, linalool, citronellol, phenylethanol, 3-(4-tert-butylphenyl)-2-methylpropanal, hexylcinnamic aldehyde, benzyl acetate, benzyl salicylate, tetrahydro-2-isobutyl-4-methyl-4(2H)-pyranol, beta ionone, methyl 2-(methylamino)benzoate, (E)-3-methyl-4-(2,6,6-trimethyl-2-cyclohexen-1-yl)-3-buten-2-one, (1E)-1-(2,6,6-trimethyl-2-cyclohexen-1-yl)-1-penten-3-one, 1-(2,6,6-trimethyl-1,3-cyclohexadien-1-yl)-2-buten-1-one, (2E)-1-(2,6,6-trimethyl-2-cyclohexen-1-yl)-2-buten-1-one, (2E)-1-[2,6,6-trimethyl-3-cyclohexen-1-yl]-2-buten-1-one, (2E)-1-(2,6,6-trimethyl-1-cyclohexen-1-yl)-2-buten-1-one, 2,5-dimethyl-2-indanmethanol, 2,6,6-trimethyl-3-cyclohexene-1-carboxylate, 3-(4,4-dimethyl-1-cyclohexen-1-yl)propanal, hexyl salicylate, 3,7-dimethyl-1,6-nonadien-3-ol, 3-(4-isopropylphenyl)-2-methylpropanal, verdyl acetate, geraniol, p-menth-1-en-8-ol, 4-(1,1-dimethylethyl)-1-cyclohexyle acetate, 1,1-dimethyl-2-phenylethyl acetate, 4-cyclohexyl-2-methyl-2-butanol, amyl salicylate, high cis methyl dihydrojasmonate, 3-methyl-5-phenyl-1-pentanol, verdyl proprionate, geranyl acetate, tetrahydro linalool, cis-7-p-menthanol, propyl (S)-2-(1,1-dimethylpropoxy)propanoate, 2-methoxynaphthalene, 2,2,2-trichloro-1-phenylethyl acetate, 4/3-(4-hydroxy-4-methylpentyl)-3-cyclohexene-1-carbaldehyde, amylcinnamic aldehyde, 8-decen-5-olide, 4-phenyl-2-butanone, isononyle acetate, 4-(1,1-dim6thyldthyl)-1-cyclohexyl acetate, verdyl isobutyrate and/or mixture of methylionones isomers, 2-Methyl-3-(3-tertbutylphenyl)propanal, 2,5,7,7-Tetramethyloctanal, 4-(1,1-dimethylethyl)phenylpropanal, 3-(4-Isopropylphenyl)propanal, octahydro-8,8-dimethylnaphthalene-2-carboxaldehyd, octahydro-4,7-methanoindanilydenebutanal, beta-methyl-3-(1-methylethyl)phenylpropanal, 2-methyl-3-(3,4-methylendioxyphenyl)propanal, 7-hydroxy-3,7-dimethyloctanal, 4-(4-hydroxy-4-methylpentyl)-3-cyclohexen-1-carboxaldehyd, 2,2-dimethyl-3-(3-methylphenyl)propanol, cis-4-(1-methylethyl)cyclohexanmethanol, 1-(4-isopropylcyclohexyl)ethanol, 3-Methyl-4-phenylbutan-2-ol, dimethylphenylpropanol, 2-methyl-3-(4-(2-methylpropyl)phenyl)propanal, 3-(4-isobutylphenyl)-2-methylpropanal, 3,4-dioxy(cycloacetonyl)toluol, 3-(1-ethoxyethoxy)-3,7-dimethyl-1,6-octadien, alpha,alpha-dimethyl-4-ethylphenylpropanal, gamma-methylphenylpentanal;

Fruity ingredients: gamma-undecalactone, 2,5-trimethyl-5-pentylcyclopentanone, 2-methyl-4-propyl-1,3-oxathiane, 4-decanolide, ethyl 2-methyl-pentanoate, hexyl acetate, ethyl 2-methylbutanoate, gamma nonalactone, allyl heptanoate, 2-phenoxyethyl isobutyrate, ethyl 2-methyl-1,3-dioxolane-2-acetate-(3,3/1,1-dimethyl-5-indanyl)propanal, diethyl 1,4-cyclohexanedicarboxylate, 3-methyl-2-hexen-1-yl acetate, 1-[3,3-dimethylcyclohexyl]ethyl [3-ethyl-2-oxiranyl]acetate and/or diethyl 1,4-cyclohexane dicarboxylate;

Green ingredients: 2-methyl-3-hexanone (E)-oxime, 2,4-dimethyl-3-cyclohexene-1-carbaldehyde, 2-tert-butyl-1-cyclohexyl acetate, styrallyl acetate, allyl (2-methylbutoxy)acetate, 4-methyl-3-decen-5-ol, diphenyl ether, (Z)-3-hexen-1-ol and/or 1-(5,5-dimethyl-1-cyclohexen-1-yl)-4-penten-1-one;

Musk ingredients: 1,4-dioxa-5,17-cycloheptadecane-dione, pentadecenolide, 3-methyl-5-cyclopentadecen-1-one, 1,3,4,6,7,8-hexahydro-4,6,6,7,8,8-hexamethyl-cyclopenta-g-2-benzopyrane, (1S,1'R)-2-[1-(3',3'-dimethyl-1'-cyclohexyl)ethoxy]-2-methylpropyl propanoate, (Z)-4-cyclopentadecen-1-one, 3-methylcyclopentadecanone, 1-oxa-12-cyclohexadecen-2-one, 1-oxa-13-cyclohexadecen-2-one, (9Z)-9-cycloheptadecen-1-one, 2-{1S)-1-[(1R)-3,3-dimethylcyclohexyl]ethoxy}-2-oxoethyl propionate, oxacyclohexadecan-2-one and/or (1S,1'R)-[1-(3',3'-dimethyl-1'-cyclohexyl)ethoxycarbonyl]methyl propanoate;

Woody ingredients: 1-[(1RS,6SR)-2,2,6-trimethylcyclohexyl]-3-hexanol, 3,3-dimethyl-5-[(1R)-2,2,3-trimethyl-3-cyclopenten-1-yl]-4-penten-2-ol, 3,4'-dimethylspiro[oxirane-2,9'-tricyclo[6.2.1.0$^{2,7}$]undec[4]ene, (1-ethoxyethoxy)cyclododecane, 2,2,9,11-tetramethylspiro[5.5]undec-8-en-1-yl acetate, 1-(octahydro-2,3,8,8-tetramethyl-2-naphtalenyl)-1-ethanone, patchouli oil, terpenes fractions of patchouli oil, Clearwood®, (1'R, E)-2-ethyl-4-(2',2',3'-trimethyl-3'-cyclopenten-1'-yl)-2-buten-1-ol, 2-ethyl-4-(2,2,3-trimethyl-3-cyclopenten-1-yl)-2-buten-1-ol, methyl cedryl ketone, 5-(2,2,3-trimethyl-3-cyclopentenyl)-3-methylpentan-2-ol, 1-(2,3,8,8-tetramethyl-1,2,3,4,6,7,8,8a-octahydronaphthalen-2-yl)ethan-1-one and/or isobornyl acetate;

Other ingredients (e.g. amber, powdery spicy or watery): dodecahydro-3a,6,6,9a-tetramethyl-naphtho[2,1-b]furan and any of its stereoisomers, heliotropin, anisic aldehyde, eugenol, cinnamic aldehyde, clove oil, 3-(1,3-benzodioxol-5-yl)-2-methylpropanal, 7-methyl-2H-1,5-benzodioxepin-3(4H)-one, 2,5,5-trimethyl-1,2,3,4,4a,5,6,7-octahydro-2-naphthalenol, 1-phenylvinyl acetate, 6-methyl-7-oxa-1-thia-4-azaspiro[4.4]nonan and/or 3-(3-isopropyl-1-phenyl)butanal.

Preferably, the invention's compounds may be used with musky, woody, ambery powdery co-ingredients, in particular with pentadecenolide, 1-(octahydro-2,3,8,8-tetramethyl-2-naphtalenyl)-1-ethanone, dodecahydro-3a,6,6,9a-tetramethyl-naphtho[2,1-b]furan and any of its stereoisomers, mixture of methylionones isomers, Methyl 2,4-dihydroxy-3,6-dimethylbenzoate, 3,3-dimethyl-5-(2,2,3-trimethyl-3-cyclopenten-1-yl)-4-penten-2-ol, mixture of 1-[2,6,10-trimethyl-1,5,9-cyclododecatrien-1-yl]ethanone, 1-[-4,8-dimethyl-12-methylene-4,8-cyclododecadien-1-yl]ethanone and 1-[-2,6,10-trimethyl-2,5,9-cyclododecatrien-1-yl]ethanone or vetiver oil.

A perfumery base according to the invention may not be limited to the above mentioned perfuming co-ingredients, and many other of these co-ingredients are in any case listed in reference texts such as the book by S. Arctander, Perfume and Flavor Chemicals, 1969, Montclair, New Jersey, USA, or its more recent versions, or in other works of a similar nature, as well as in the abundant patent literature in the field of perfumery. It is also understood that said co-ingredients may also be compounds known to release in a controlled manner various types of perfuming compounds also known as properfume or profragrance. Non-limiting examples of suitable properfume may include 4-(dodecylthio)-4-(2,6,6-trimethyl-2-cyclohexen-1-yl)-2-butanone, 4-(dodecylthio)-4-(2,6,6-trimethyl-1-cyclohexen-1-yl)-2-butanone, trans-3-(dodecylthio)-1-(2,6,6-trimethyl-3-cyclohexen-1-yl)-1-butanone, 2-phenylethyl oxo(phenyl)acetate or a mixture thereof.

By "perfumery adjuvant" we mean here an ingredient capable of imparting additional added benefit such as a color, a particular light resistance, chemical stability, etc. A detailed description of the nature and type of adjuvant commonly used in perfuming composition cannot be exhaustive, but it has to be mentioned that said ingredients are well known to a person skilled in the art. One may cite as specific non-limiting examples the following: viscosity agents (e.g. surfactants, thickeners, gelling and/or rheology modifiers), stabilizing agents (e.g. preservatives, antioxidant, heat/light and or buffers or chelating agents, such as BHT), coloring agents (e.g. dyes and/or pigments), preservatives (e.g. antibacterial or antimicrobial or antifungal or anti irritant agents), abrasives, skin cooling agents, fixatives, insect repellants, ointments, vitamins and mixtures thereof.

It is understood that a person skilled in the art is perfectly able to design optimal formulations for the desired effect by admixing the above mentioned components of a perfuming composition, simply by applying the standard knowledge of the art as well as by trial and error methodologies.

An invention's composition consisting of at least one compound of formula (I) and at least one perfumery carrier consists of a particular embodiment of the invention as well as a perfuming composition comprising at least one compound of formula (I), at least one perfumery carrier, at least one perfumery base, and optionally at least one perfumery adjuvant.

According to a particular embodiment, the compositions mentioned above, comprise more than one compound of formula (I) and enable the perfumer to prepare accords or perfumes possessing the odor tonality of various compounds of the invention, creating thus new building block for creation purposes.

For the sake of clarity, it is also understood that any mixture resulting directly from a chemical synthesis, e.g. a reaction medium without an adequate purification, in which the compound of the invention would be involved as a starting, intermediate or end-product could not be considered as a perfuming composition according to the invention as far as said mixture does not provide the inventive compound in a suitable form for perfumery. Thus, unpurified reaction mixtures are generally excluded from the present invention unless otherwise specified.

The invention's compound can also be advantageously used in all the fields of modern perfumery, i.e. fine or functional perfumery, to positively impart or modify the odor of a consumer product into which said compound (I) is added. Consequently, another object of the present invention consists of by a perfumed consumer product comprising, as a perfuming ingredient, at least one compound of formula (I), as defined above.

The invention's compound can be added as such or as part of an invention's perfuming composition.

For the sake of clarity, "perfumed consumer product" is meant to designate a consumer product which delivers at least a pleasant perfuming effect to the surface or space to which it is applied (e.g. skin, hair, textile, or home surface). In other words, a perfumed consumer product according to the invention is a perfumed consumer product which comprises a functional formulation, as well as optionally additional benefit agents, corresponding to the desired consumer product, and an olfactive effective amount of at least one invention's compound. For the sake of clarity, said perfumed consumer product is a non-edible product.

The nature and type of the constituents of the perfumed consumer product do not warrant a more detailed description here, which in any case would not be exhaustive, the skilled person being able to select them on the basis of his general knowledge and according to the nature and the desired effect of said product.

Non-limiting examples of suitable perfumed consumer products include a perfume, such as a fine perfume, a splash or eau de parfum, a cologne or a shave or after-shave lotion; a fabric care product, such as a liquid or solid detergent, a fabric softener, a liquid or solid scent booster, a fabric refresher, an ironing water, a paper, a bleach, a carpet cleaner, a curtain-care product; a body-care product, such as a hair care product (e.g. a shampoo, a coloring preparation or a hair spray, a color-care product, a hair shaping product, a dental care product), a disinfectant, an intimate care product; a cosmetic preparation (e.g. a skin cream or lotion, a vanishing cream or a deodorant or antiperspirant (e.g. a spray or roll on), a hair remover, a tanning or sun or after sun product, a nail product, a skin cleansing, a makeup); or a skin-care product (e.g. a soap, a shower or bath mousse, oil or gel, or a hygiene product or a foot/hand care products); an air care product, such as an air freshener or a "ready to use" powdered air freshener which can be used in the home space (rooms, refrigerators, cupboards, shoes or car) and/or in a public space (halls, hotels, malls, etc.); or a home care product, such as a mold remover, a furnisher care product, a wipe, a dish detergent or a hard-surface (e.g. a floor, bath, sanitary or a window-cleaning) detergent; a leather care product; a car care product, such as a polish, a wax or a plastic cleaner.

Some of the above-mentioned perfumed consumer products may represent an aggressive medium for the invention's compounds, so that it may be necessary to protect the latter from premature decomposition, for example by encapsulation or by chemically binding it to another chemical which is suitable to release the invention's ingredient upon a suitable external stimulus, such as an enzyme, light, heat or a change of pH.

The proportions in which the compounds according to the invention can be incorporated into the various aforementioned products or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.0001% to 10% by weight, or even more, of the compounds of the invention based on the weight of the composition into which they are incorporated. In the case of perfumed consumer product, typical concentrations are in the order of 0.00001% to 1% by weight, or even more, of the compounds of the invention based on the weight of the consumer product into which they are incorporated.

A further object of the present invention is a composition of matter comprising
a) 0.1 to 50% w/w of (1R,3S,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane;
b) 10 to 99.9% w/w of compound of formula (I) as defined above; and
c) 20 to 80% w/w of (3R,3aR,6R,7S,8aS)-3,6,8,8-tetramethylhexahydro-1H-3a,7-methanoazulen-5(4H)-one;
the percentage being relative to the total weight of the composition of matter.

According to any embodiment of the invention, the composition of matter comprises 15 to 30% w/w of (1R,3S,7R,8R,10S,13R)-5,7,9,9,13-pentamethyl-5-[(1E)-1-propen-1-yl]-4,6-dioxatetracyclo[6.5.1.0$^{1,10}$.0$^{3,7}$]tetradecane.

According to any embodiment of the invention, the composition of matter comprises 15 to 50% w/w of compound of formula (I) as defined above According to any embodiment of the invention, the composition of matter comprises compound of formula (I) being (1R,3S,7R,8R,10S,13R)-5-methoxy-7,9,9,13-tetramethyl-4,6-dioxatetracyclo[6.5.1.0$^{1,10}$.0$^{3,7}$]tetradecane.

EXAMPLES

The invention will now be described in further detail by way of the following examples, wherein the abbreviations have the usual meaning in the art, the temperatures are indicated in degrees centigrade (° C.); the NMR spectral data were recorded in CDCl$_3$ (if not stated otherwise) with a 360 or 400 MHz machine for $^1$H and $^{13}$C, the chemical shifts δ are indicated in ppm with respect to TMS as standard, the coupling constants J are expressed in Hz.

Example 1

Synthesis of (1R,3S,5S,7R,8R,10S,13R)-5-methoxy-7,9,9,13-tetramethyl-4,6-dioxatetracyclo [6.5.1.0$^{1,10}$.0$^{3,7}$]tetradecane and (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane A 250 mL 3-neck round bottomed flask equipped with a magnetic stir bar and reflux condenser was charged with 2.5 g of cedrenediol, 1.65 g of trimethylortho formate, 0.012 g of Amberlyst 15 and 75 mL of dichloromethane. The mixture was stirred at room temperature for 2.5 h, then filtered and quenched by pouring the filtrate into saturated $NaHCO_3$. The reaction mixture was extracted twice with $CH_2Cl_2$, washed three times with water, dried over $Na_2SO_4$ and concentrated on the rotovap to give 2.2 g of crude concentrate containing 50% of a diastereomeric mixture of 5-methoxy-7,9,9,13-tetramethyl-4,6-dioxatetracyclo[6.5.1.0$^{1,10}$.0$^{3,7}$]tetradecane ((1R,3S,5R,7R,8R,10S,13R)/(1R,3S,5S,7R,8R,10S,13R)=54/46). The crude was chromatographed on silica with 95/5 pentane/ether to give 2 principal fractions. The first, 0.27 g, was composed of 35% of (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane and 62% of cedranone. The second, 0.075 g, contained 87% of 1R,3S,5S,7R,8R,10S,13R)-5-methoxy-7,9,9,13-tetramethyl-4,6-dioxatetracyclo[6.5.1.0$^{1,10}$.0$^{3,7}$]tetradecane. The latter was bulb-to-bulb distilled to give 60 mg of 90% pure (1R,3S,5S,7R,8R,10S,13R)-5-methoxy-7,9,9,13-tetramethyl-4,6-dioxatetracyclo[6.5.1.0$^{1,10}$.0$^{3,7}$]tetradecane. The mixture containing (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane and cedranone was diluted in 20 mL of ether and treated with $LiAlH_4$ to transform the cedranone into cedrol. After workup, the reaction mixture was separated by silica column chromatography (95/5 pentane/ether) to give 41 mg of 81% pure (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane.

$^1$H-NMR (600 MHz, $CDCl_3$): δ (ppm) 0.82 (d, J 7.2 Hz, 3H), 1.03 (s, 3H), 1.15 (s, 3H), 1.25-1.34 (m, 2H), 1.38-1.48 (m, 1H), 1.5-1.66 (m, 6H), 1.70-1.77 (m, 1H), 1.81-1.91 (m, 2H), 1.94-2.02 (m, 2H), 3.40 (s, 3H), 4.18 (t, J 5.8 Hz, 1H), 5.76 (s, 1H)

$^{13}$C (150 MHz, $CDCl_3$): δ (ppm) 15.4, 25.4, 26.6, 28.5, 30.6, 36.1, 38.8, 39.7, 41.7, 42.6, 52.1, 53.3, 57.2, 76.8, 77.0, 77.2, 78.4, 83.6, 116.8

Example 2

Synthesis of (1R,3S,7R,8R,10S,13R)-5-ethoxy-7,9,9,13-tetramethyl-4,6-dioxatetracyclo[6.5.1.0$^{1,10}$.0$^{3,7}$]tetradecane A 3-neck 250 mL round bottomed flask equipped with a magnetic stir bar and reflux condenser was placed under $N_2$ atmosphere and charged with 5 g of cedrenediol, 150 mL of cyclohexane and 6.2 g of trimethylorthoformate. The stirred suspension was charged with 10 mg of TMSOTf in one shot and stirred for 30 minutes to complete conversion of the cedrenediol into products. The reaction mixture was poured into 90 g of saturated $NaHCO_3$ and the reaction flask was rinsed with 50 mL of ether. After phase separation, the organic layer was dried over $Na_2SO_4$ and concentrated on the rotovap to give 7.8 g of crude containing 77% of a 6/4 diastereomeric mixture of the desired orthoester. The latter was chromatographed on silica using a pentane/ether gradient of 95/5 to 80/20 to give 6.1 g of 91% pure (1R,3S,7R,8R,10S,13R)-5-ethoxy-7,9,9,13-tetramethyl-4,6-dioxatetracyclo[6.5.1.0$^{1,10}$.0$^{3,7}$]tetradecane. After distilling the chromatographed material on the kuegel-rohr, 4.7 g of 92% pure (1R,3S,7R,8R,10S,13R)-5-ethoxy-7,9,9,13-tetramethyl-4,6-dioxatetracyclo[6.5.1.0$^{1,10}$.0$^{3,7}$]tetradecane was obtained with a (1R,3S,5R,7R,8R,10S,13R)/(1R,3S,5S,7R,8R,10S,13R) ratio of 39/54.

$^1$H-NMR (600 MHz, Pyridine-$d_5$): δ (ppm) 0.77 (t, J 7 Hz, 6H), 0.95 (d, J 6.4 Hz, 6H), 1.06 (s, 6H), 1.14-1.25 (m, 8H), 1.28-1.56 (m, 13H), 1.58-1.81 (m, 6H), 1.88-1.97 (m, 2H), 1.97-2.07 (m, 3H), 2.12 (dd, J 12.1 Hz, 7.4 Hz, 1H), 2.39 (d, 11.7 Hz, 1H), 3.66-3.77 (m, 4H), 4.07 (t, 8 Hz, 1H), 4.26 (t, 8 Hz, 1H), 6.02 (s, 1H), 6.07 (s, 1H)

$^{13}$C (150 MHz, Pyridine-$d_5$): δ (ppm) 150.12, 149.91, 149.69, 135.71, 135.51, 135.32, 123.71, 123.51, 123.31, 117.00, 116.58, 86.01, 83.41, 78.74, 76.95, 61.70, 61.61, 57.6, 57.54, 57.4, 57.31, 53.04, 52.33, 42.69, 42.53, 41.93, 41.79, 40.40, 39.90, 39.12, 38.82, 36.17, 36.09, 30.39, 30.36, 28.46, 27.09, 25.99, 25.54, 25.52, 15.61, 15.58, 15.56, 15.53

Example 3

Synthesis of (1R,3S,7R,8R,10S,13R)-5-n-propoxy-7,9,9,13-tetramethyl-4,6-dioxatetracyclo[6.5.1.0$^{1,10}$.0$^{3,7}$]tetradecane A 3-neck 250 mL round bottomed flask equipped with a magnetic stir bar and reflux condenser was placed under $N_2$ atmosphere and charged with 5 g of cedrenediol, 150 mL of cyclohexane and 8 g of tripropylorthoformate. The stirred suspension was charged with 10 mg of TMSOTf in one shot and stirred for 30 minutes to complete conversion of the cedrenediol into products. The reaction mixture was poured into 90 g of saturated $NaHCO_3$ and the reaction flask was rinsed with 50 mL of ether. After phase separation, the organic layer was dried over $Na_2SO_4$ and concentrated on the rotovap to give 6.2 g of crude containing 79% of a 6/4 diastereomeric mixture of the desired (1R,3S,7R,8R,10S,13R)-5-n-propoxy-7,9,9,13-tetramethyl-4,6-dioxatetracyclo[6.5.1.0$^{1,10}$.0$^{3,7}$]tetradecane. The latter was chromatographed on silica using a pentane/ether gradient of 95/5 to 80/20 to give 5.4 g of 85% pure (1R,3S,7R,8R,10S,13R)-5-n-propoxy-7,9,9,13-tetramethyl-4,6-dioxatetracyclo[6.5.1.0$^{1,10}$.0$^{3,7}$]tetradecane contaminated with 13% of cedranone. After distilling the chromatographed material on the kuegel-rohr, 4.7 g of 92% pure (1R,3S,7R,8R,10S,13R)-5-n-propoxy-7,9,9,13-tetramethyl-4,6-dioxatetracyclo[6.5.1.0$^{1,10}$.0$^{3,7}$]tetradecane was obtained. In order to remove the cedranone, the chromatographed material was dissolved into dry ether and charged with 0.3 g of $LiAlH_4$ and reacted for 30 minutes before quenching. After working up the reaction, 5.5 g of 87% pure (1R,3S,7R,8R,10S,13R)-5-n-propoxy-7,9,9,13-tetramethyl-4,6-dioxatetracyclo[6.5.1.0$^{1,10}$.0$^{3,7}$]tetradecane was obtained. The latter was re-chromatographed using 9/1 pentane/ether to give 4.40 g of 93% pure product. After kuegel-rohr distillation, 4.2 g of (1R,3S,7R,8R,10S,13R)-5-n-propoxy-7,9,9,13-tetramethyl-4,6-dioxatetracyclo[6.5.1.0$^{1,10}$.0$^{3,7}$]tetradecane was obtained with a (1R,3S,5R,7R,8R,10S,13R)/(1R,3S,5S,7R,8R,10S,13R) ratio of 41/59.

$^1$H-NMR (600 MHz, Pyridine-$d_5$): δ (ppm) 0.78 (d, J 7.1 Hz, 6H), 0.91 (t, J 7.7 Hz, 6H), 0.95 (d, 8.4 Hz, 6H), 1.06 (s, 6H), 1.14-1.25 (m, 8H), 1.15-1.26 (m, 2H), 1.30-1.55 (m, 2H), 1.57-1.80 (m, 10H), 1.89-1.97 (m, 2H), 1.98-2.07 (m, 3H), 2.13 (dd, J 12.1 Hz, 7.4 Hz, 1H), 2.39 (d, 11.7 Hz, 1H), 3.54-3.67 (m, 4H), 4.08 (t, 8 Hz, 1H), 4.26 (t, 8 Hz, 1H), 6.02 (s, 1H), 6.07 (s, 1H)

$^{13}$C (150 MHz, Pyridine-$d_5$): δ (ppm) 150.12, 149.91, 149.69, 135.71, 135.51, 135.32, 123.71, 123.51, 123.31, 117.07, 116.70, 86.07, 83.39, 78.76, 76.97, 67.81, 67.62, 57.73, 57.61, 57.46, 57.41, 52.95, 52.34, 42.70, 42.45, 42.07, 41.79, 40.38, 39.91, 39.12, 38.85, 36.25, 36.17, 30.39, 30.35, 28.50, 28.47, 27.06, 26.08, 25.62, 25.52, 23.41, 23.40, 15.55, 15.54, 10.95, 10.88

Example 4

Synthesis of (1R,3S,7R,8R,10S,13R)-5-n-prop-2-enoxy-7,9,9,13-tetramethyl-4,6-dioxatetracyclo[6.5.1.0$^{1,10}$.0$^{3,7}$]tetradecane A 3-neck 100 mL round bottomed flask equipped with a magnetic stir bar and reflux condenser was placed under $N_2$ atmosphere and charged with 2 g of cedrenediol, 60 mL of heptane and 6.2 g of triallylorthoformate (prepared according to *Finn. Chem. Lett.* 1979, 47). The stirred suspension was cooled to −15° C. with a water/$CaCl_2$) bath and charged with 100 mg of TMSOTf in one shot and stirred for 30 minutes then quenched by adding 0.5 g of triethylamine. After stirring the reaction for an additional 15 minutes, 30 mL of saturated $NaHCO_3$ was added, followed by 50 mL of ether. The organic phase was dried over $Na_2SO_4$ and concentrated on the rotovap to give 6.7 g of crude containing 19% of a 7/3 diastereomeric mixture of the desired (1R,3S,7R,8R,10S,13R)-5-n-prop-2-enoxy-7,9,9,13-tetramethyl-4,6-dioxatetracyclo[6.5.1.0$^{1,10}$.0$^{3,7}$]tetradecane along with 54% of triallylorthoformate and 21% of cedranone. The crude was carefully distilled on the kuegel-rohr (140-160° C./0.05 mbar) to give a fraction containing 0.5 g of 82% pure (1R,3S,7R,8R,10S,13R)-5-n-prop-2-enoxy-7,9,9,13-tetramethyl-4,6-dioxatetracyclo[6.5.1.0$^{1,10}$.0$^{3,7}$]tetradecane at 82% purity and 0.7 g of residue containing 93% (1R,3S,7R,8R,10S,13R)-5-n-prop-2-enoxy-7,9,9,13-tetramethyl-4,6-dioxatetracyclo[6.5.1.0$^{1,10}$.0$^{3,7}$]tetradecane. Both the residue from the pot and the 0.5 g of distilled material were combined and chromatographed on water-pre-treated silica using a pentane/ether gradient of pure pentane to 90/10 to give 0.6 g of 93% pure (1R,3S,7R,8R,10S,13R)-5-n-prop-2-enoxy-7,9,9,13-tetramethyl-4,6-dioxatetracyclo[6.5.1.0$^{1,10}$.0$^{3,7}$]tetradecane. After distillation on the kuegel-rohr, 0.6 g of 93% pure material composed of two diastereomers with an (1R,3S,5R,7R,8R,10S,13R)/(1R,3S,5S,7R,8R,10S,13R) ratio of 7/3.

$^1$H-NMR (600 MHz, Benzene-d$_6$): δ (ppm) 0.72-0.95 (m, 10H), 1.11-1.47 (m, 8H), 1.52-1.88 (m, 4H), 1.96 (dd, 17.4 Hz, 4.2 Hz, 1H), 2.20 (dd, 13 Hz, 7.3 Hz, 1H), 2.48 (d, 11.9 Hz, 1H), 3.85 (t, 8.3 Hz, 1H), 3.96-4.13 (m, 3H), 5.0 (dd, 10.4 Hz, 1.6 Hz, 1H), 5.29 (dd, 17.2 Hz, 1.8 Hz, 1H), 5.79-5.92 (m, 2H)

$^{13}$C (150 MHz, Benzene-d$_6$): δ (ppm) 134.98, 134.93, 128.31, 128.19, 128.10, 128.02, 127.94, 127.86, 116.89, 116.461, 116.031, 115.96, 86.16, 83.49, 78.79, 77.12, 67.01, 66.86, 57.78, 57.61, 57.55, 57.42, 52.98, 52.26, 42.57, 42.35, 42.06, 41.88, 40.39, 40.11, 39.19, 38.90, 36.28, 36.25, 30.48, 30.45, 28.52, 28.49, 26.99, 26.18, 25.61, 25.52, 15.59, 15.55

Example 5

Synthesis of (1R,3S,7R,8R,10S,13R)-5-n-but-3-enoxy-7,9,9,13-tetramethyl-4,6-dioxatetracyclo[6.5.1.0$^{1,10}$.0$^{3,7}$]tetradecane A 3-neck 100 mL round bottomed flask equipped with a magnetic stir bar and reflux condenser was placed under $N_2$ atmosphere and charged with 2 g of cedrenediol, 60 mL of heptane and 7.6 g of tri-but-3-enylorthoformate. The stirred suspension was cooled to between −30 to −15° C. and charged with 60 mg of TMSOTf in one shot and stirred for 30 minutes then quenched by adding 0.5 mL of triethylamine. After stirring the reaction for an additional 10 minutes, 30 mL of saturated $NaHCO_3$ was added, followed by 50 mL of ether. The organic phase was dried over $Na_2SO_4$ and concentrated on the rotovap to give 8.25 g of crude containing 32% of a 6/4 diastereomeric mixture of the desired (1R,3S,7R,8R,10S,13R)-5-n-but-3-enoxy-7,9,9,13-tetramethyl-4,6-dioxatetracyclo[6.5.1.0$^{1,10}$.0$^{3,7}$]tetradecane along with 62% of tri-but-3-enylorthoformate. The crude was distilled on the kuegel-rohr (120-160° C./0.05 mbar) to give two fractions: 5.73 g containing 91% pure (1R,3S,7R,8R,10S,13R)-5-n-but-3-enoxy-7,9,9,13-tetramethyl-4,6-dioxatetracyclo[6.5.1.0$^{1,10}$.0$^{3,7}$]tetradecane and a second fraction containing 2.13 g of 94% pure (1R,3S,7R,8R,10S,13R)-5-n-but-3-enoxy-7,9,9,13-tetramethyl-4,6-dioxatetracyclo[6.5.1.0$^{1,10}$.0$^{3,7}$]tetradecane as a 38/62 mixture (1R,3S,5R,7R,8R,10S,13R)/(1R,3S,5S,7R,8R,10S,13R).

$^1$H-NMR (600 MHz, Benzene-d$_6$): δ (ppm) 0.76 (d, J 7.4 Hz, 1H), 0.81 (d, J 7.4, 2H), 0.85 (s, 1H), 0.87 (s, 2H), 0.91 (d, 8 Hz, 3H), 1.12-1.20 (m, 1H), 1.22-1.46 (m, 7H), 1.54-1.75 (m, 4H), 1.76-1.86 (m, 1H), 1.96 (dd, 14.7 Hz, 4.4 Hz, 1H), 2.18 (dd, 13.3 Hz, 6.9 Hz, 1H), 2.24-2.35 (m, 2H), 2.46 (d, 12.1 Hz, 1H), 3.47-3.62 (m, 2H), 3.84 (t, 8.1 Hz, 1H), 4.0 (t, 7.6 Hz, 1H), 4.97-5.0 (m, 2H), 5.75-5.86 (m, 1H), 5.874 (s, 1H), 5.878 (s, 1H)

$^{13}$C (150 MHz, Benzene-d$_6$): δ (ppm) 135.57, 135.54, 128.19, 128.02, 127.94, 127.86, 117.19, 116.72, 116.42, 86.02, 83.37, 78.69, 77.06, 65.63, 65.49, 57.85, 57.65, 57.58, 57.47, 52.96, 52.26, 42.56, 42.32, 42.15, 41.91, 40.36, 40.09, 39.22, 38.92, 36.33, 36.30, 34.64, 34.63, 30.47, 30.46, 28.55, 28.50, 27.00, 26.17, 25.64, 25.54, 15.60, 15.57

Example 6

Synthesis of (1R,3S,7R,8R,10S,13R)-5-methoxy-5,7,9,9,13-pentamethyl-4,6-dioxatetracyclo[6.5.1.0$^{1,10}$.0$^{3,7}$]tetradecane A 3-neck 100 mL round bottomed flask equipped with a magnetic stir bar and reflux condenser was placed under $N_2$ atmosphere and charged with 2 g of cedrenediol, 50 mL of cyclohexane and 5 g of trimethylorthoacetate. The stirred suspension was cooled to 0° C. and charged with 20 mg of TMSOTf in one shot and stirred for 45 minutes then quenched by adding 5 g of triethylamine. After stirring the reaction for an additional 10 minutes, the reaction mixture was concentrated on the rotovap to give 2.75 g of crude. The latter was re-dissolved into ether, washed with saturated $NaHCO_3$, dried over $Na_2SO_4$ and concentrated on the rotovap to give 3.3 g of product which was chromatographed on basic alumina to afford 1.86 g of (1R,3S,7R,8R,10S,13R)-5-methoxy-5,7,9,9,13-pentamethyl-4,6-dioxatetracyclo[6.5.1.0$^{1,10}$.0$^{3,7}$]tetradecane. After distilling on the kuegel-rohr, 1.8 g of distillate was collected composed of an 87/13 (1R,3S,5R,7R,8R,10S,13R)/(1R,3S,5S,7R,8R,10S,13R) mixture of two diastereomers.

$^1$H-NMR (600 MHz, Pyridine-d$_5$): δ (ppm) 0.77 (d, J 7 Hz, 4H), 0.91 (t, J 7.7 Hz, 6H), 0.95 (s, 4H), 1.06 (s, 4H), 1.16-1.26 (m, 2H), 1.28-1.40 (m, 2H), 1.41-2.04 (m, 20H), 2.26 (dd, J 12.7 Hz, 6.8 Hz, 1H), 2.39 (d, 11.7 Hz, 1H), 3.36 (s, 3H), 3.38 (s, 3H), 4.14 (dd, 9.1 Hz, 6 Hz, 1H), 4.26 (dd, 8.5 Hz, 6.5 Hz, 1H)

$^{13}$C (150 MHz, Pyridine-d$_5$): δ (ppm) 150.09, 149.91, 149.73, 135.68, 135.52, 135.35, 123.68, 123.51, 123.35, 122.40, 86.97, 78.96, 58.02, 57.63, 52.69, 50.63, 42.44, 42.10, 39.73, 38.80, 35.98, 30.7907, 28.51, 27.30, 25.55, 23.75, 15.57

Example 7

Synthesis of (1R,3S,7R,8R,10S,13R)-5-ethoxy-5,7,9,9,13-pentamethyl-4,6-dioxatetracyclo[6.5.1.0$^{1,10}$.0$^{3,7}$]tetradecane A 3-neck 250 mL round bottomed flask equipped with a magnetic stir bar and reflux condenser was placed under $N_2$ atmosphere and charged with 5 g of cedrenediol, 150 mL of cyclohexane and 17 g of triethylorthoacetate. The stirred suspension was cooled to 0° C. and charged with 100 mg of TMSOTf in one shot and stirred for 35 minutes then quenched by adding 5 g of triethylamine. After stirring the reaction for an additional 10 minutes, the reaction mixture was concentrated on the rotovap to give 7.28 g of crude. The latter was re-dissolved into ether, washed with saturated NaHCO$_3$, dried over Na$_2$SO$_4$ then chromatographed on basic alumina using 9/1 pentane/ether to afford 7.2 g of (1R,3S,7R,8R,10S,13R)-5-ethoxy-5,7,9,9,13-pentamethyl-4,6-dioxatetracyclo[6.5.1.0$^{1,10}$.0$^{3,7}$]tetradecane. After distilling on the kuegel-rohr, 4.58 g of distillate was collected composed of an 70/30 (1R,3S,5R,7R,8R,10S,13R)/(1R,3S,5S,7R,8R,10S,13R) mixture of two diastereomers.

$^1$H-NMR (600 MHz, Pyridine-d$_5$): δ (ppm) 0.77 (d, J 7.2 Hz, 1H), 0.81 (d, J 7.2 Hz, 3H), 0.96 (overlapping s, 4H), 1.16-1.27 (m, 6H), 1.28-1.41 (m, 2H), 1.43-1.54 (m, 8H), 1.55-1.86 (m, 11H), 1.89-2.06 (m, 2H), 2.33 (dd, J 12.8 Hz, 6.9 Hz, 1H), 2.42 (d, J 11.8 Hz, 1H), 3.61-3.70 (m, 3H), 4.15 (dd, 8.9 Hz, 6.5 Hz, 1H), 4.26 (dd, 8.4 Hz, 6.6 Hz, 1H)

$^{13}$C (150 MHz, Pyridine-d$_5$): δ (ppm) 150.08, 149.90, 149.72, 135.70, 135.53, 135.37, 123.81, 123.69, 123.52, 123.36, 121.91, 121.45, 86.85, 85.42, 79.36, 78.88, 58.85, 58.72, 58.60, 58.10, 57.98, 57.88, 52.44, 52.35, 42.60, 42.57, 42.16, 41.91, 41.26, 39.81, 38.82, 38.76, 36.56, 35.93, 30.80, 30.74, 28.69, 28.59, 27.34, 26.84, 25.83, 25.47, 24.53, 24.45, 15.78, 15.68, 15.56

Example 8

Synthesis of (1R,3S,7R,8R,10S,13R)-5-ethoxy-5-ethyl-7,9,9,13-tetramethyl-4,6-dioxatetracyclo[6.5.1.0$^{1,10}$.0$^{3,7}$]tetradecane A 3-neck 100 mL round bottomed flask equipped with a magnetic stir bar and reflux condenser was placed under $N_2$ atmosphere and charged with 2 g of cedrenediol, 50 mL of cyclohexane and 7.4 g of triethylorthopropionate. The stirred suspension was cooled to 0° C. and charged with 10 mg of TMSOTf in one shot and stirred for 35 minutes then quenched by adding 1 mL of triethylamine. After stirring the reaction for an additional 10 minutes, the reaction mixture was washed with saturated NaHCO$_3$, dried over Na$_2$SO$_4$ and concentrated on the rotovap to give 4 g of crude. The latter was chromatographed on silica using 95/5 pentane/ether to afford 1.6 g of (1R,3S,7R,8R,10S,13R)-5-ethoxy-5-ethyl-7,9,9,13-tetramethyl-4,6-dioxatetracyclo[6.5.1.0$^{1,10}$.0$^{3,7}$]tetradecane. After distilling on the kuegel-rohr, 1.57 g of distillate was collected comprised of an 80/20 (1R,3S,5R,7R,8R,10S,13R)/(1R,3S,5S,7R,8R,10S,13R) mixture of two diastereomers.

$^1$H-NMR (600 MHz, Pyridine-d$_5$): δ (ppm) 0.82 (d, J 7.1 Hz, 3H), 0.96 (s, 4H), 1.04-1.27 (m, 15H), 1.28-1.39 (m, 2H), 1.39-1.56 (m, 8H), 1.67 (quintet, 7.3 Hz, 2H), 1.72-1.87 (m, 4H), 1.88-2.03 (m, 5H), 2.34 (dd, J 12.8 Hz, 6.8 Hz, 1H), 2.41 (d, 11.6 Hz, 1H), 3.60 (q, 7.1 Hz, 2H), 4.13 (dd, 9.1 Hz, 6.8 Hz, 1H), 4.27 (dd, 8.6 Hz, 6.1 Hz, 1H)

$^{13}$C (150 MHz, Pyridine-d$_5$): δ (ppm) 150.09, 149.91, 149.73, 135.68, 135.51, 135.35, 123.68, 123.51, 123.35, 86.64, 79.12, 78.73, 58.80, 58.39, 58.17, 58.12, 58.06, 57.95, 52.42, 42.65, 42.61, 42.16, 41.91, 41.44, 39.97, 38.77, 38.68, 36.56, 35.85, 30.84, 30.80, 30.18, 30.10, 28.71, 28.59, 27.55, 27.03, 25.83, 25.44, 15.56, 8.75

Example 9

Synthesis of (1R,3S,7R,8R,10S,13R)-5-prop-2-enoxy-5,7,9,9,13-pentamethyl-4,6-dioxatetracyclo[6.5.1.0$^{1,10}$.0$^{3,7}$]tetradecane 50 mL 3-neck round bottomed flask equipped with a magnetic stir bar and air condenser was charged with 2 g of cedrenediol, 10 g of of triallylorthoacetate and 20 mL of heptane. The slurry was cooled under $N_2$ to −60° C. in an iPrOH/CO$_2$ bath then charged with 40 μL of TMSOTf in one shot. The reaction mixture remained a slurry and no conversion was observed. It was then allowed to warm to 0° C. over a 1.5 h period whereby the reaction mixture became homogeneous and was immediately quenched with the addition of 1 g of triethyl amine. After removing solvent on the rotovap, 10.43 g of crude concentrate was obtained. The latter was carefully distilled on the on the kuegel-rohr (1.7 mbar/60-80° C.) to remove unreacted triallyorthoacetate to afford 6.4 g of distillate comprised of 98% triallylorthoacetate and 2.9 g of residue. The residue was chromatographed on water-pre-treated silica using 20/1 pentane-ether to give 2.6 g of material which was carefully distilled on the kuegel-rohr to give 1.2 g of 92% pure (1R,3S,7R,8R,10S,13R)-5-prop-2-enoxy-5,7,9,9,13-pentamethyl-4,6-dioxatetracyclo[6.5.1.0$^{1,10}$.0$^{3,7}$]tetradecane as a 77/23 (1R,3S,5R,7R,8R,10S,13R)/(1R,3S,5S,7R,8R,10S,13R) mixture of diastereomers.

$^1$H-NMR (600 MHz, Pyridine-d$_5$): δ (ppm) 0.8 (d, J 7.2 Hz, 3H), 0.954-0.958 (pair of overlapping s, 4H), 1.06-1.08 (pair of overlapping s, 4H), 1.22 (quintet, 6 Hz, 2H), 1.29-1.39 (m, 2H), 1.41-1.53 (m, 7H), 1.57-1.87 (m, 10H), 1.96-2.04 (m, 3H), 2.32 (dd, J 12.8 Hz, 6.8 Hz, 1H), 2.43 (d, 11.7 Hz, 1H), 4.16 (dd, J 9 Hz, 6.9 Hz, 1H), 4.19-4.25 (m, 1H), 5.16 (dd, J 10.4 Hz, 1.8 Hz, 1H), 5.45 (dd, J 17.2 Hz, 2.1 Hz, 1H), 5.99-6.09 (m, 1H)

$^{13}$C (150 MHz, Pyridine-d$_5$): δ (ppm) 150.25, 150.09, 149.91, 149.73, 135.92, 135.81, 135.68, 135.59, 135.52, 135.36, 123.81, 123.68, 123.52, 123.35, 123.15, 122.09, 115.39, 115.17, 87.14, 79.54, 78.99, 64.62, 64.19, 58.58, 58.13, 57.87, 57.82, 52.51, 52.33, 42.61, 42.43, 42.21, 41.90, 41.20, 39.78, 38.77, 38.72, 36.42, 35.92, 30.78, 30.76, 28.64, 28.58, 27.37, 26.84, 25.75, 25.72, 25.47, 24.61, 24.51, 15.56

Example 10

Synthesis of (1R,3S,7R,8R,10S,13R)-5,7,9,9,13-pentamethyl-5-{[2-propen-1-yloxy]methyl}-4,6-dioxatetracyclo[6.5.1.0$^{1,10}$.0$^{3,7}$]tetradecane 25 mL 3-neck round bottomed flask equipped with a magnetic stir bar and reflux condenser under $N_2$ atmosphere was charged with 786 mg of the acetate prepared from the previous step, 15 mL of anhydrous ether and cooled to 0° C. To this solution, 115 mg of LiAlH$_4$ was added in portions, stirred for 1 h then quenched by sequentially adding 120 mg of water, 150 mg of 15% NaOH and 350 mg of water. The resulting slurry was filtered over celite and the filtrate was concentrated on the rotovap to give 748 mg of solid ((3aS, 4aR,5R,9R,9aR)-2,5,8,8,9a-pentamethyloctahydro-4H-4a, 9-methanoazuleno[5,6-d][1,3]dioxol-2-yl)methanol at 97% purity as 72/28 mixture of two diastereomers. The crude product was used in the next step without further purification.

25 mL 3-neck round bottomed flask equipped with a magnetic stir bar and reflux condenser under $N_2$ atmosphere was charged with 150 mg of 60% NaH and 10 mL of anhydrous THF. To this slurry, 0.55 g of the crude alcohol ((3aS,4aR,5R,9R,9aR)-2,5,8,8,9a-pentamethyloctahydro-4H-4a,9-methanoazuleno[5,6-d][1,3]dioxol-2-yl)methanol prepared from the previous step was slowly added then heated for 30 minutes at 50° C., after which the reaction mixture was cooled room temperature and charged with 920 mg of allyl bromide in one shot. The reaction was re-heated to 50° C. and stirred at that temperature for 15 h, then quenched by pouring it into 30 mL of ice water. After diluting the quenched reaction mixture with ether, the aqueous phase was extracted once with ether and the extracts were combined, washed with water, dried over $Na_2SO_4$ and concentrated on the rotovap to give 577 mg of 77% pure allylated product (1R,3S,7R,8R,10S,13R)-5,7,9,9,13-pentamethyl-5-[{2-propen-1-yloxy]methyl}-4,6-dioxatetracyclo[6.5.1.01,10.03,7]tetradecane composed of 75/25 mixture of 2 diastereomers. The latter was chromatographed on silica using 95/5 pentane-ether to give 0.35 g of 97% pure material. After distilling on the kuegel-rohr, 0.34 g of 98% pure product was obtained as 75/25 (1R,3S,5R,7R,8R,10S, 13R)/(1R,3S,5S,7R,8R,10S,13R) mixture of two diastereomers.

$^1$H-NMR (600 MHz, Benzene-$d_6$): δ (ppm) 0.75 (d, J 7 Hz, 3H), 0.78 (d, J 7 Hz, 3H), 0.882 (s, 3H), 0.888 (s, 3H), 0.95 (s, 3H), 1.14-1.21 (m, 1H), 1.25-1.33 (m, 2H), 1.35-1.47 (m, 2H), 1.48 (s, 2H), 1.53 (s, 2H), 1.57-1.67 (m, 6H), 1.98 (d, 4.7 Hz, 1H), 1.99 (d, 4.4 Hz, 1H), 2.23 (d, 12.1 Hz, 1H), 3.59-3.70 (m, 2H), 3.94 (t, 7.4 Hz, 1H), 3.96-4.05 (m, 2H), 5.04, 5.06 (doublet of quartets, 2 Hz, 1.9 Hz, 1H), 5.28 (q, 2.2 Hz, 1H), 5.31 (q, 2.2 Hz, 1H)

$^{13}$C (150 MHz, Benzene-$d_6$): δ (ppm) 135.68, 135.61, 128.32, 128.31, 128.30, 128.29, 128.19, 128.11, 128.03, 127.95, 127.87, 127.72, 127.71, 127.71, 116.23, 116.01, 109.92, 85.18, 78.77, 78.60, 77.53, 76.66, 72.28, 72.25, 58.72, 58.66, 57.86, 57.80, 52.53, 42.38, 42.36, 42.32, 42.21, 41.97, 41.64, 38.90, 38.75, 36.24, 36.15, 31.17, 31.14, 28.78, 28.75, 28.17, 28.10, 26.08, 25.63, 25.59, 25.81, 15.36, 15.41

Example 11

Synthesis of (1R,3S,7R,8R,10S,13R)-5,7,9,9,13-pentamethyl-5-{[1-propen-1-yloxy]methyl}-4,6-dioxatetracyclo[6.5.1.0$^{1,10}$.0$^{3,7}$]tetradecane 100 mL 3-neck round bottomed flask equipped with a magnetic stir bar and air condenser was charged with 30 mL of toluene, 150 mg of Ru-COD-pivalate catalyst and heated under $N_2$ to 100° C. 1.2 g of (1R,3S,7R,8R,10S,13R)-5,7, 9,9,13-pentamethyl-5-{[2-propen-1-yloxy]methyl}-4,6-dioxatetracyclo[6.5.1.01,10.03,7]tetradecane dissolved in 20 mL of toluene was then added over a 1 h period. After a total of 3.5 h, the dark reaction mixture was cooled with an ice water bath, concentrated on the rotovap and chromatographed on silica using a 8/2 pentane/ether mixture to give 1.2 g of a 98% mixture of four isomers of (1R,3S,7R,8R, 10S,13R)-5,7,9,9,13-pentamethyl-5-{[1-propen-1-yloxy] methyl}-4,6-dioxatetracyclo[6.5.1.01,10.03,7]tetradecane. After distilling on the kuegel-rohr, 0.8 g of 98% pure product (1R,3S,7R,8R,10S,13R)-5,7,9,9,13-pentamethyl-5-{[1-propen-1-yloxy]methyl}-4,6-dioxatetracyclo[6.5.1.0$^1$, 1.03-7]tetradecane was obtained as a mixture of four diastereomers: 68% (1R,3S,5R,7R,8R,10S,13R)-5,7,9,9,13-pentamethyl-5-{[1-propen-1-yloxy]methyl}-4,6-dioxatetracyclo[6.5.1.0$^{1,10}$.0$^{3,7}$]tetradecane (E/Z=85/15), 32% (1R,3S,5S,7R,8R,10S,13R)-5,7,9,9,13-pentamethyl-5-{[1-propen-1-yloxy]methyl}-4,6-dioxatetracyclo [6.5.1.0$^{1,10}$.0$^{3,7}$] (E/Z=87/13).

$^1$H-NMR (600 MHz, Benzene-$d_6$): δ (ppm) 0.74 (d, J 7.1 Hz, 3H), 0.872, 0.875 (pair of overlapping singlets, 3H), 0.941, 0.948 (pair of overlapping s, 3H), 1.12-1.20 (m, 1H), 1.24-1.32 (m, 1H), 1.33-1.47 (m, 8H), 1.50 (s, 1H), 1.57-1.77 (m, 7H), 1.80 (dd, 9 Hz, 1.8 Hz, 1H), 1.82 (dd, 9 Hz, 2.5 Hz, 1H), 1.96 (d, 2.5 Hz, 1H), 1.98 (d, 4.6 Hz, 1H), 2.17 (d, 10.5 Hz, 1H), 3.71-3.85 (m, 2H), 3.93 (dd, 8.9 Hz, 6.8 Hz, 1H), 3.99 (dd, 9.2 Hz, 6.7 Hz, 1H), 4.76-4.85 (m, 1H), 6.33 (dd, 12.5 Hz, 1.4 Hz, 1H)

$^{13}$C (150 MHz, Benzene-$d_6$): δ (ppm) 147.54, 147.43, 128.31, 128.19, 128.10, 128.03, 127.95, 127.87, 109.10, 98.56, 98.51, 85.34, 78.87, 78.75, 76.30, 75.49, 58.65, 57.76, 57.70, 52.50, 52.49, 42.38, 42.35, 42.23, 42.18, 41.95, 41.60, 38.86, 38.74, 36.17, 36.13, 31.13, 28.73, 28.72, 28.07, 28.06, 26.03, 25.59, 25.57, 25.25, 15.60, 15.57, 12.66, 12.64

Example 12

Synthesis of (1R,3S,7R,8R,10S,13R)-5,7,9,9,13-pentamethyl-5-{[acetoxy]methyl}-4,6-dioxatetracyclo[6.5.1.0$^{1,10}$.0$^{3,7}$]tetradecane a) Preparation of Acetoxyacetone 250 mL 3-neck round bottomed flask equipped with a magnetic stir bar and reflux condenser under $N_2$ atmosphere was charged with 130 mL of $CH_2Cl_2$, 28 g of acetic anhydride, 0.7 g of DMAP followed by the addition of 17 g of hydroxyacetone dissolved in 20 mL of $CH_2Cl_2$ over a 15 minute period. The reaction was allowed to react for an additional 1 h then quenched by carefully pouring the reaction mixture into saturated $NaHCO_3$. After phase separation, the aqueous phase was extracted 3× with $CH_2Cl_2$ and the combined organic extracts were dried over $Na_2SO_4$. Upon removal of the solvent on the rotovap (40° C./500 mbar), 30 g of crude 1-acetoxy-2-propanone was obtained which was then distilled on the kuegel-rohr to afford 18 g of 90% pure acetoxyacetone.

b) Preparation of Acetoxyacetone Dimethylacetal 25 mL 3-neck round bottomed flask equipped with a magnetic stir bar and reflux condenser under $N_2$ atmosphere was charged with 1.1 g of acetoxyacetone, 10 mL of methanol, 10 mg of p-TSA followed by the addition of 1.1 g of trimethylorthoformate over a 25 minute period. The reaction was allowed to react for an additional 1 h then quenched with saturated $NaHCO_3$. After workup and solvent removal on the rotovap (40° C./400 mbar), 1.8 g of crude was obtained which was then distilled on the kuegel-rohr (10 mbar/100° C.) to afford 1.28 g of acetoxyacetone dimethylacetal at 96% purity.

$^1$H-NMR (600 MHz, Benzene-$d_6$): δ (ppm) 1.26 (s, 3H), 1.65 (s, 3H), 3.00 (s, 6H), 4.17 (s, 2H)

$^{13}$C (150 MHz, Benzene-$d_6$): δ (ppm) 128.20, 128.04, 127.88, 114.81, 99.64, 64.43, 50.93, 20.29 c) Preparation of (1R,3S,7R,8R,10S,13R)-5,7,9,9,13-pentamethyl-5-{[acetoxy]methyl}-4,6-dioxatetracyclo[6.5.1.0$^{1,10}$.0$^{3,7}$]tetradecane 25 mL 3-neck round bottomed flask equipped with a magnetic stir bar and Dean-Stark distillation apparatus was charged with 1.28 g of acetoxyacetone dimethylacetal, 15 mL of cyclohexane, 1 g of cedrenediol, 32 mg of p-toluenelsulfonic acid and refluxed under $N_2$ atmosphere for 1 h. The reaction mixture was cooled to room temperature and poured into 20 g of saturated $NaHCO_3$, phase separated, extracted with ether, dried over $Na_2SO_4$ and concentrated on the rotovap to give 1.69 g of product at 69% purity as a 72/28 mixture of two diastereomers. The latter was chromatographed with silica using a pentane/ether gradient starting from 90% to 85% pentane to afford 1.02 g of 99% product (1R,3S,7R,8R,10S,13R)-5,7,9,9,13-pentamethyl-5-{[acetoxy]methyl}-4,6-dioxatetracyclo[6.5.1.0$^{1,10}$.0$^{3,7}$]tetradecane. After distillation on the kuegel-rohr, 948 mg pure (1R,3S,7R,8R,10S,13R)-5,7,9,9,13-pentamethyl-5-{[acetoxy]methyl}-4,6-dioxatetracyclo[6.5.1.0$^{1,10}$.0$^{3,7}$]tetradecane was obtained as a 72/28 (1R,3S,5R,7R,8R,10S,13R)/(1R,3S,5S,7R,8R,10S,13R) mixture of 2 diastereomers.

$^1$H-NMR (600 MHz, Benzene-$d_6$): δ (ppm) 0.74 (d, J 7.2 Hz, 3H), 0.78 (d, J 7.2 Hz, 3H), 0.843 (s, 3H), 0.849 (s, 3H), 0.89 (s, 3H), 0.92 (s, 3H), 1.11-1.19 (m, 1H), 1.23-1.30 (m, 2H), 1.33-1.45 (m, 2H), 1.47 (s, 2H), 1.49 (s, 2H), 1.57-1.65 (m, 6H), 1.66-1.82 (m, 6H), 1.94 (d, 4.7 Hz, 1H), 1.96 (d, 4.4 Hz, 1H), 2.16 (d, 12.1 Hz, 1H), 2.20 (d, 12.1 Hz, 1H), 3.90 (dd, 8.8 Hz, 6.7 Hz, 1H), 3.99 (t, 8.3 Hz, 1H), 4.33 (d, 11.4 Hz, 1H), 4.47 (d, 11 Hz, 1H)

$^{13}$C (150 MHz, Benzene-$d_6$): δ (ppm) 128.19, 128.03, 127.87, 108.13, 107.99, 85.68, 85.50, 79.11, 78.89, 69.96, 69.10, 58.68, 58.59, 57.71, 57.60, 52.48, 52.47, 42.39, 42.35, 42.19, 42.15, 41.66, 41.53, 38.80, 38.67, 36.19, 36.10, 31.14, 31.06, 28.70, 28.07, 27.78, 26.11, 25.61, 25.54, 25.33, 20.49, 15.60, 15.57

Example 13

Biodegradability Measurement of the Invention's Compound and Comparative Compound The biodegradation assessment was carried out using the OECD 301F ('manometric respirometry') biodegradation test under identical conditions with sludge inoculum originating from the same wastewater treatment plant as follows.

Mineral medium was prepared from stock solutions according to the OECD guideline (OECD, 1992): 100 mL of solution A (8.50 g/L $KH_2PO_4$, 21.75 g/L $K_2HPO_4$, 33.40 g/L $Na_2HPO_4 \times 2\ H_2O$, 0.50 g/L $NH_4Cl$), 10 mL of solution B (27.50 g/L $CaCl_2$)), 10 mL of solution C (22.50 g/L $MgSO_4 \times 7\ H_2O$) and 10 mL of solution D (0.25 g/L $FeCl_3 \times 6\ H_2O$) were mixed, the volume adjusted to 10 L with demineralized water and the pH adjusted to 7.4.

Activated sludge was collected from the sewage plant at Villette (Thônex, Switzerland), which treats predominantly domestic wastewaters. The sample was filtered on a polypropylene 149 μm pore size filter (Spectrum Laboratories, Rancho Dominguez, USA), washed three times by centrifugation at 3000×g for 30 min at room temperature and suspended in the same volume of medium. The suspension was stirred and maintained under pure oxygen at room temperature overnight. The test material was dispersed directly in the final volume of medium (100 mL) to give a test concentration of 100 mg/L and then inoculated in the test flask with 30 mg/L dry weight of sludge. Use was made of duplicates containing inoculum only and duplicates containing test substance plus inoculum.

The samples were magnetically stirred and incubated in diffuse light at 22±1° C. On day 30, all manometric data were collected. The manometric device OxitopC (WTW, Weilheim, Germany) calculated automatically the oxygen consumption. The percentage of biodegradation was calculated as described in the OECD 301F guideline (Organisation for Economic Co-operation and Development (OECD), 1992. OECD Guideline for testing of chemicals, Degradation and accumulation, No. 301: Ready biodegradability).

The test in duplicates was conducted with each compound; i.e. (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane (invention's compound), (1R,3S,7R,8R,10S,13R)-5-methoxy-7,9,9,13-tetramethyl-4,6-dioxatetracyclo[6.5.1.0$^{1,10}$.0$^{3,7}$]tetradecane (invention's compound), (1R,3S,7R,8R,10S,13R)-5-methoxy-5,7,9,9,13-pentamethyl-4,6-dioxatetracyclo[6.5.1.0$^{1,10}$.0$^{3,7}$]tetradecane (invention's compound) and (1R,3S,7R,8R,10S,13R)-5-(methoxymethyl)-5,7,9,9,13-pentamethyl-4,6-dioxatetracyclo[6.5.1.0$^{1,10}$.0$^{3,7}$]tetradecane (prior art compound). The results are shown in FIG. 1 which corresponds to an average of the duplicates.

The invention's compounds, (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane, (1R,3S,7R,8R,10S,13R)-5-methoxy-7,9,9,13-tetramethyl-4,6-dioxatetracyclo[6.5.1.0$^{1,10}$.0$^{3,7}$]tetradecane and (1R,3S,7R,8R,10S,13R)-5-methoxy-5,7,9,9,13-pentamethyl-4,6-dioxatetracyclo[6.5.1.0$^{1,10}$.0$^{3,7}$]tetradecane, were biodegradable within 30 days with a percentage of degradation reaching more than 60% whereas (1R,3S,7R,8R,10S,13R)-5-(methoxymethyl)-5,7,9,9,13-pentamethyl-4,6-dioxatetracyclo[6.5.1.0$^{1,10}$.0$^{3,7}$]tetradecane did not biodegrade. In other words, the invention's compounds, unexpectedly and despite of the structure similarity, were biodegradable compounds.

Example 14

Preparation of a Perfuming Composition

A perfuming composition for a men fine fragrance, dosed at 15% in the final product, was prepared by admixing the following ingredients:

| Ingredient | Parts by weight |
|---|---|
| Ambrox ®[1]) super | 80 |
| Amyl salicylate | 80 |
| 10%* ethyl 2-methylpentanoate | 80 |

-continued

| Ingredient | Parts by weight |
|---|---|
| Citronellol | 80 |
| Clearwood ®[2] | 100 |
| 4-cyclohexyl-2-methyl-2-butanol | 400 |
| Coumarin | 80 |
| Damascone alpha | 10 |
| Dihydromyrcenol | 400 |
| Floralozone[3] | 10 |
| Habanolide ®[4] | 800 |
| Hedione ®[5] HC | 1000 |
| (+−)-3-(1,3-benzodioxol-5-yl)-2-methylpropanal | 100 |
| Helvetolide ®[6] | 200 |
| Hivernal ®[7] | 20 |
| Iso E ® super[8] | 2400 |
| Lavender oil | 80 |
| Lemon oil | 400 |
| 6,6-dimethoxy-2,5,5-trimethyl-2-hexene | 160 |
| Methyl 2,4-dihydroxy-3,6-dimethylbenzoate | 100 |
| 10%* neobutenone ®[9] alpha | 80 |
| Nirvanol ®[10] | 100 |
| Patchouli oil | 300 |
| Pink pepper oil | 80 |
| (Z)-3-hexen-1-ol | 10 |
| (3Z)-3-hexen-1-yl salicylate | 80 |
| Rhubofix ®[11] | 10 |
| Scentenal ®[12] | 10 |
| Sclareolate ®[13] | 200 |
| (+−)-1-phenylethyl acetate | 40 |
| (+−)-2-ethyl-4,4-dimethylcyclohexanone | 10 |
| Mixture of 1-[2,6,10-trimethyl-1,5,9-cyclododecatrien-1-yl]ethanone, 1-[-4,8-dimethyl-12-methylene-4,8-cyclododecadien-1-yl]ethanone and 1-[-2,6,10-trimethyl-2,5,9-cyclododecatrien-1-yl]ethanone | 200 |
| 2-tert-butyl-1-cyclohexyl acetate | 200 |
| Vetyver oil | 100 |
| Dipropylene glycol | 2000 |
| | 10000 |

*in dipropyleneglycol
[1](−)-(8R)-8,12-epoxy-13,14,15,16-tetranorlabdane; origin: Firmenich SA, Geneva, Switzerland
[2]origin: Firmenich SA, Geneva, Switzerland
[3]3-(4/2-Ethylphenyl)-2,2-dimethylpropanal; origin: International Flavors & Fragrances, USA
[4]Pentadecenolide; origin: Firmenich SA, Geneva, Switzerland
[5]dihydrojasmonate with high amount of cis isomer; origin: Firmenich SA, Geneva, Switzerland
[6](1S,1'R)-2-[1-(3',3'-dimethyl-1'-cyclohexyl)ethoxy]-2-methylpropyl propanoate; origin: Firmenich SA, Geneva, Switzerland
[7]3-(3,3/1,1-dimethyl-5-indanyl)propanal; origin: Firmenich SA, Geneva, Switzerland
[8]1-(octahydro-2,3,8,8-tetramethyl-2-naphtalenyl)-1-ethanone; origin: International Flavors & Fragrances, USA
[9]1-(5,5-dimethyl-1-cyclohexen-1-yl)-4-penten-1-one; origin: Firmenich SA, Geneva, Switzerland
[10]3,3-dimethyl-5-(2,2,3-trimethyl-3-cyclopenten-1-yl)-4-penten-2-ol; origin: Firmenich SA, Geneva, Switzerland
[11](+−)-3,4'-dimethylspiro[oxirane-2,9'-tricyclo[6.2.1.0$^{2,7}$]undec[4]ene; origin: Firmenich SA, Geneva, Switzerland
[12]8(9)-methoxy-tricyclo[5.2.1.0.(2,6)]decane-3(4)-carbaldehyde; origin: Firmenich SA, Geneva, Switzerland
[13]Propyl (S)-2-(1,1-dimethylpropoxy)propanoate; origin: Firmenich SA, Geneva, Switzerland The addition of 400 parts by weight of (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane to replace 400 parts by weight of dipropylene glycol in the above-described composition imparted to the latter a reinforced woody-dry and ambery connotation.

Similar effect was obtained when a same amount of (1R,3S,5S,7R,8R,10S,13R)-5-methoxy-7,9,9,13-tetramethyl-4,6-dioxatetracyclo[6.5.1.0$^{1,10}$.0$^{3,7}$]tetradecane or (1R,3S,7R,8R,10S,13R)-5-methoxy-5,7,9,9,13-pentamethyl-4,6-dioxatetracyclo[6.5.1.0$^{1,10}$.0$^{3,7}$]tetradecane or (1R,3S,7R,8R,10S,13R)-5-ethoxy-5,7,9,9,13-pentamethyl-4,6-dioxatetracyclo[6.5.1.0$^{1,10}$.0$^{3,7}$]tetradecane or a mixture comprising (1R,3S,5R,7R,8R,10S,13R)-5-methoxy-7,9,9,13-tetramethyl-4,6-dioxatetracyclo[6.5.1.0$^{1,10}$.0$^{3,7}$]tetradecane and (1R,3S,5S,7R,8R,10S,13R)-5-methoxy-7,9,9,13-tetramethyl-4,6-dioxatetracyclo[6.5.1.0$^{1,10}$.0$^{3,7}$]tetradecane with a (1R,3S,5R,7R,8R,10S,13R)/(1R,3S,5S,7R,8R,10S,13R) ratio of 57/41 was used to replace 400 parts by weight of dipropylene glycol.

The invention claimed is:

1. A compound of formula

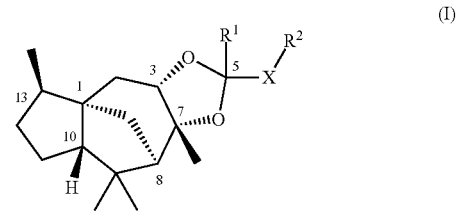

in the form of any one of its stereoisomers or as a mixture thereof, and wherein $R^1$ represents a hydrogen atom, a $C_{1-3}$ alkyl group or $C_{2-3}$ alkenyl group; X represents an oxygen atom when $R^2$ represents a $C_{1-4}$ alkyl group or $C_{2-4}$ alkenyl group or X represents a $CH_2$—O group when $R^2$ represents a $C_{2-4}$ alkenyl group or a MeC=O group.

2. The compound according to claim 1, characterized in that X represents an oxygen atom.

3. The compound according to claim 1, characterized in that $R^1$ represents a hydrogen atom or a methyl group.

4. The compound according to claim 1, characterized in that $R^2$ represents a methyl or an ethyl group.

5. The compound according to claim 1, characterized in that the compound of formula (I) is in the form of a mixture of isomers comprising at least 55% of isomers with a R configuration on carbon 5 and at most 45% of isomers with a S configuration on carbon 5.

6. The compound according to claim 1, characterized in that the compound of formula (I) is (1R,3S,5R,7R,8R,10S,13R)-5-methoxy-7,9,9,13-tetramethyl-4,6-dioxatetracyclo[6.5.1.0$^{1,10}$.0$^{3,7}$] tetradecane, (1R,3S,5S,7R,8R,10S,13R)-5-methoxy-7,9,9,13-tetramethyl-4,6-dioxatetracyclo[6.5.1.0$^{1,10}$.0$^{3,7}$] tetradecane, or a mixture thereof, (1R,3S,7R,8R,10S,13R)-5-methoxy-5,7,9,9,13-pentamethyl-4,6-dioxatetracyclo [6.5.1.0$^{1,10}$.0$^{3,7}$] tetradecane and (1R,3S,7R,8R,10S,13R)-5-ethoxy-5,7,9,9,13-pentamethyl-4,6-dioxatetracyclo [6.5.1.0$^{1,10}$.0$^{3,7}$] tetradecane.

7. A method of using a compound of formula (I) as defined in claim 1, the method comprising using the compound of formula (I) as a perfuming ingredient.

8. A method to confer, enhance, improve, or modify the odor properties of a perfuming composition or of a perfumed article, which method comprises adding to said composition or article an effective amount of at least a compound of formula (I) as defined in claim 1.

9. A perfuming composition comprising:
i) at least one compound of formula (I), as defined in claim 1;
ii) at least one ingredient selected from the group consisting of a perfumery carrier and a perfumery base; and
iii) optionally at least one perfumery adjuvant.

10. A perfumed consumer product comprising at least one compound of formula (I), as defined in claim 1.

11. The perfumed consumer product according to claim 10, characterized in that the perfumery consumer product is a perfume, a fabric care product, a body-care product, a cosmetic preparation, a skin-care product, an air care product or a home care product.

12. The perfumed consumer product according to claim 11, characterized in that the perfumery consumer product is a fine perfume, a splash or eau de parfum, a cologne, a shave or after-shave lotion, a liquid or solid detergent, a fabric softener, a fabric refresher, an ironing water, a paper, a bleach, a carpet cleaner, a curtain-care product, a shampoo, a coloring preparation, a color care product, a hair shaping product, a dental care product, a disinfectant, an intimate care product, a hair spray, a vanishing cream, a deodorant or antiperspirant, a hair remover, a tanning or sun product, a nail product, a skin cleansing, a makeup, a perfumed soap, a shower or bath mousse, an oil or a gel, or a foot/hand care product, a hygiene product, an air freshener, a "ready to use" powdered air freshener, a mold remover, a furnisher care, a wipe, a dish detergent or a hard-surface detergent, a leather care product, a car care product.

13. A composition of matter comprising
a) 0.1 to 50% w/w of (1R,3S,7R,8R, 10S, 13R)-5,7,9,9, 13-pentamethyl-5-[(1E)-1-propen-1-yl]-4,6-dioxatetracyclo [$6.5.1.0^{1,10}.0^{3,7}$] tetradecane;
b) 10 to 99.9% w/w of compound of formula (I) as defined in claim 1; and
c) 20 to 80% w/w of (3R,3aR,6R,7S,8aS)-3,6,8,8-tetramethylhexahydro-1H-3a,7-methanoazulen-5 (4H)-one;
the percentage being relative to the total weight of the composition of matter.

14. A perfumed consumer product comprising a perfuming composition as defined in claim 9.

15. The perfumed consumer product according to claim 14, characterized in that the perfumery consumer product is a perfume, a fabric care product, a body-care product, a cosmetic preparation, a skin-care product, an air care product or a home care product.

* * * * *